United States Patent
Hume et al.

(10) Patent No.: US 11,839,187 B2
(45) Date of Patent: Dec. 12, 2023

(54) *EPICHLOË* ENDOPHYTE

(71) Applicants: Grasslanz Technology Limited, Lincoln (NZ); The Grains Research and Development Corporation, Barton (AU)

(72) Inventors: David Edward Hume, Palmerston North (NZ); Wayne Roydon Simpson, Palmerston North (NZ); Richard David Johnson, Palmerston North (NZ)

(73) Assignees: GRASSLANZ TECHNOLOGY LIMITED, Lincoln (NZ); THE GRAINS RESEARCH AND DEVELOPMENT CORPORATION, Barton (AU)

( * ) Notice: Subject to any disclaimer, the term of this patent is extended or adjusted under 35 U.S.C. 154(b) by 440 days.

(21) Appl. No.: 16/971,657

(22) PCT Filed: Feb. 19, 2019

(86) PCT No.: PCT/IB2019/051304
§ 371 (c)(1),
(2) Date: Aug. 20, 2020

(87) PCT Pub. No.: WO2019/162816
PCT Pub. Date: Aug. 29, 2019

(65) Prior Publication Data
US 2021/0068364 A1 Mar. 11, 2021

(30) Foreign Application Priority Data

Feb. 21, 2018 (NZ) ........................................ 740056
Jun. 15, 2018 (NZ) ........................................ 743525

(51) Int. Cl.
*A01H 17/00* (2006.01)
*A01N 63/30* (2020.01)
*A01H 15/00* (2006.01)
*C12N 1/14* (2006.01)
*C12Q 1/6895* (2018.01)
*C12R 1/645* (2006.01)

(52) U.S. Cl.
CPC ............. *A01H 17/00* (2013.01); *A01H 15/00* (2013.01); *A01N 63/30* (2020.01); *C12N 1/14* (2013.01); *C12Q 1/6895* (2013.01); *C12N 1/145* (2021.05); *C12Q 2600/156* (2013.01); *C12R 2001/645* (2021.05)

(58) Field of Classification Search
CPC ................................ A01H 17/00; A01H 15/00
See application file for complete search history.

(56) References Cited

U.S. PATENT DOCUMENTS

2016/0262335 A1* 9/2016 Hume .................... C12N 1/145

OTHER PUBLICATIONS

Environmental Protection Authority Application No. APP201774 Applicant: Grasslanz Technology Ltd and AgResearch Ltd (Year: 2012).*
Wayne Roydon Simpson Doctor of Philosophy in Plant Biology Thesis Massey University, Palmerston North, New Zealand "Hordeeae Epichloe endophytes and the formation of synthetic symbioses with cereal grasses" (Year: 2016).*
Card et al FEMS Microbiology and Ecoology vol. 88, pp. 94-106 (Year: 2014).*

* cited by examiner

*Primary Examiner* — David H Kruse
(74) *Attorney, Agent, or Firm* — Lewis Kohn & Walker LLP; David M. Kohn; Kari Moyer-Henry

(57) ABSTRACT

The present invention relates to isolated strains of *Epichloë* endophytes that form symbiotic associations with host plants, wherein the symbiotic associations are combinations of endophytes and host plants that are not found in nature. The invention also relates to combinations of host plants and *Epichloë* endophytes that are not found in nature, methods of making such combinations and methods of conferring at least some level of pest resistance on a host plant using such endophytes.

21 Claims, 2 Drawing Sheets

Specification includes a Sequence Listing.

SEQUENCE LISTING

```
<160> NUMBER OF SEQ ID NOS: 46

<210> SEQ ID NO 1
<211> LENGTH: 18
<212> TYPE: DNA
<213> ORGANISM: Artificial Sequence
<220> FEATURE:
<223> OTHER INFORMATION: Primer

<400> SEQUENCE: 1
tgtaaaacga cggccagt                                                 18

<210> SEQ ID NO 2
<211> LENGTH: 7
<212> TYPE: DNA
<213> ORGANISM: Artificial Sequence
<220> FEATURE:
<223> OTHER INFORMATION: Primer

<400> SEQUENCE: 2 gtttctt                                                              7

<210> SEQ ID NO 3
<211> LENGTH: 24
```

-continued

```
<212> TYPE: DNA
<213> ORGANISM: Artificial Sequence
<220> FEATURE:
<223> OTHER INFORMATION: Primer

<400> SEQUENCE: 3
cgctcagggc tacatacacc atgg                                          24

<210> SEQ ID NO 4
<211> LENGTH: 23
<212> TYPE: DNA
<213> ORGANISM: Artificial Sequence
<220> FEATURE:
<223> OTHER INFORMATION: Primer

<400> SEQUENCE: 4
ctcatcgagt aacgcaggcg acg                                           23

<210> SEQ ID NO 5
<211> LENGTH: 24
<212> TYPE: DNA
<213> ORGANISM: Artificial Sequence
<220> FEATURE:
<223> OTHER INFORMATION: Primer

<400> SEQUENCE: 5
catggatgga caagagattg cacg                                          24

<210> SEQ ID NO 6
<211> LENGTH: 24
<212> TYPE: DNA
<213> ORGANISM: Artificial Sequence
<220> FEATURE:
<223> OTHER INFORMATION: Primer

<400> SEQUENCE: 6
ttcactgcta caattctgtc cagc                                          24

<210> SEQ ID NO 7
<211> LENGTH: 21
<212> TYPE: DNA
<213> ORGANISM: Artificial Sequence
<220> FEATURE:
<223> OTHER INFORMATION: Primer

<400> SEQUENCE: 7
cacaaagaca aacgccaaaa g                                             21

<210> SEQ ID NO 8
<211> LENGTH: 22
<212> TYPE: DNA
<213> ORGANISM: Artificial Sequence
<220> FEATURE:
<223> OTHER INFORMATION: Primer

<400> SEQUENCE: 8
gcaaagctca cagacaaagg tc                                            22

<210> SEQ ID NO 9
<211> LENGTH: 21
<212> TYPE: DNA
<213> ORGANISM: Artificial Sequence
<220> FEATURE:
<223> OTHER INFORMATION: Primer

<400> SEQUENCE: 9
```
tacctctgca cggtgtattc c                                              21

<210> SEQ ID NO 10
<211> LENGTH: 24
<212> TYPE: DNA
<213> ORGANISM: Artificial Sequence
<220> FEATURE:
<223> OTHER INFORMATION: Primer

<400> SEQUENCE: 10
tgcataacac tcaccttata gtcg                                           24

<210> SEQ ID NO 11
<211> LENGTH: 22
<212> TYPE: DNA
<213> ORGANISM: Artificial Sequence
<220> FEATURE:
<223> OTHER INFORMATION: Primer

<400> SEQUENCE: 11
gcgttgagga ggctagatag aa                                             22

<210> SEQ ID NO 12
<211> LENGTH: 22
<212> TYPE: DNA
<213> ORGANISM: Artificial Sequence
<220> FEATURE:
<223> OTHER INFORMATION: Primer

<400> SEQUENCE: 12
ttccaagctg aacaaaagtc aa                                             22

<210> SEQ ID NO 13
<211> LENGTH: 22
<212> TYPE: DNA
<213> ORGANISM: Artificial Sequence
<220> FEATURE:
<223> OTHER INFORMATION: Primer

<400> SEQUENCE: 13
atttgcagca gagatgatgt gt                                             22

<210> SEQ ID NO 14
<211> LENGTH: 22
<212> TYPE: DNA
<213> ORGANISM: Artificial Sequence
<220> FEATURE:
<223> OTHER INFORMATION: Primer

<400> SEQUENCE: 14
cctgcaccgg actgttagta at                                             22

<210> SEQ ID NO 15
<211> LENGTH: 24
<212> TYPE: DNA
<213> ORGANISM: Artificial Sequence
<220> FEATURE:
<223> OTHER INFORMATION: Primer

<400> SEQUENCE: 15
gatgacgtat cttgatgcta ccac                                           24

<210> SEQ ID NO 16
<211> LENGTH: 24
<212> TYPE: DNA
<213> ORGANISM: Artificial Sequence

```
<220> FEATURE:
<223> OTHER INFORMATION: Primer

<400> SEQUENCE: 16
cgtgtataaa gttcgggatc ctat                                          24

<210> SEQ ID NO 17
<211> LENGTH: 24
<212> TYPE: DNA
<213> ORGANISM: Artificial Sequence
<220> FEATURE:
<223> OTHER INFORMATION: Primer

<400> SEQUENCE: 17
gagatatccc gtctcctgat ctaa                                          24

<210> SEQ ID NO 18
<211> LENGTH: 24
<212> TYPE: DNA
<213> ORGANISM: Artificial Sequence
<220> FEATURE:
<223> OTHER INFORMATION: Primer

<400> SEQUENCE: 18
cacagcgtta cactatcaac ttcc                                          24

<210> SEQ ID NO 19
<211> LENGTH: 24
<212> TYPE: DNA
<213> ORGANISM: Artificial Sequence
<220> FEATURE:
<223> OTHER INFORMATION: Primer

<400> SEQUENCE: 19
cactaaacac acccaagaac aaga                                          24

<210> SEQ ID NO 20
<211> LENGTH: 24
<212> TYPE: DNA
<213> ORGANISM: Artificial Sequence
<220> FEATURE:
<223> OTHER INFORMATION: Primer

<400> SEQUENCE: 20
agacaggtaa gaagttttcc cctt                                          24

<210> SEQ ID NO 21
<211> LENGTH: 24
<212> TYPE: DNA
<213> ORGANISM: Artificial Sequence
<220> FEATURE:
<223> OTHER INFORMATION: Primer

<400> SEQUENCE: 21
agctttccaa tgacgacata cata                                          24

<210> SEQ ID NO 22
<211> LENGTH: 24
<212> TYPE: DNA
<213> ORGANISM: Artificial Sequence
<220> FEATURE:
<223> OTHER INFORMATION: Primer

<400> SEQUENCE: 22
taatttaggg tagcattttc tccg                                          24
```

```
<210> SEQ ID NO 23
<211> LENGTH: 24
<212> TYPE: DNA
<213> ORGANISM: Artificial Sequence
<220> FEATURE:
<223> OTHER INFORMATION: Primer

<400> SEQUENCE: 23
ggtccctatt ctaatgcagg tatg                                          24

<210> SEQ ID NO 24
<211> LENGTH: 24
<212> TYPE: DNA
<213> ORGANISM: Artificial Sequence
<220> FEATURE:
<223> OTHER INFORMATION: Primer

<400> SEQUENCE: 24
cagtgtacgg gactttgtca atac                                          24

<210> SEQ ID NO 25
<211> LENGTH: 24
<212> TYPE: DNA
<213> ORGANISM: Artificial Sequence
<220> FEATURE:
<223> OTHER INFORMATION: Primer

<400> SEQUENCE: 25
tgtataataa acatggcgtg ctct                                          24

<210> SEQ ID NO 26
<211> LENGTH: 24
<212> TYPE: DNA
<213> ORGANISM: Artificial Sequence
<220> FEATURE:
<223> OTHER INFORMATION: Primer

<400> SEQUENCE: 26
gtgttgaaag ttgttggatc actc                                          24

<210> SEQ ID NO 27
<211> LENGTH: 24
<212> TYPE: DNA
<213> ORGANISM: Artificial Sequence
<220> FEATURE:
<223> OTHER INFORMATION: Primer

<400> SEQUENCE: 27
cgaaattgta gactatgttg gagc                                          24

<210> SEQ ID NO 28
<211> LENGTH: 24
<212> TYPE: DNA
<213> ORGANISM: Artificial Sequence
<220> FEATURE:
<223> OTHER INFORMATION: Primer

<400> SEQUENCE: 28
gtagatgtat tttgagcagg gctt                                          24

<210> SEQ ID NO 29
<211> LENGTH: 24
<212> TYPE: DNA
<213> ORGANISM: Artificial Sequence
<220> FEATURE:
<223> OTHER INFORMATION: Primer
```

```
<400> SEQUENCE: 29
gagtgagacc cggtgtagta agtc                                          24

<210> SEQ ID NO 30
<211> LENGTH: 24
<212> TYPE: DNA
<213> ORGANISM: Artificial Sequence
<220> FEATURE:
<223> OTHER INFORMATION: Primer

<400> SEQUENCE: 30
gagtcattct tcgtccattg tctt                                          24

<210> SEQ ID NO 31
<211> LENGTH: 24
<212> TYPE: DNA
<213> ORGANISM: Artificial Sequence
<220> FEATURE:
<223> OTHER INFORMATION: Primer

<400> SEQUENCE: 31
gaaatgaggc gtctatctta aagc                                          24

<210> SEQ ID NO 32
<211> LENGTH: 24
<212> TYPE: DNA
<213> ORGANISM: Artificial Sequence
<220> FEATURE:
<223> OTHER INFORMATION: Primer

<400> SEQUENCE: 32
tttcttgatt tccaaagaac aaca                                          24

<210> SEQ ID NO 33
<211> LENGTH: 24
<212> TYPE: DNA
<213> ORGANISM: Artificial Sequence
<220> FEATURE:
<223> OTHER INFORMATION: Primer

<400> SEQUENCE: 33
cagtcatcga ttaaaagtga gcat                                          24

<210> SEQ ID NO 34
<211> LENGTH: 24
<212> TYPE: DNA
<213> ORGANISM: Artificial Sequence
<220> FEATURE:
<223> OTHER INFORMATION: Primer

<400> SEQUENCE: 34
atgtcatctg cttcaacaag agtc                                          24

<210> SEQ ID NO 35
<211> LENGTH: 24
<212> TYPE: DNA
<213> ORGANISM: Artificial Sequence
<220> FEATURE:
<223> OTHER INFORMATION: Primer

<400> SEQUENCE: 35
tcttccatac aatttcttcc cttc                                          24

<210> SEQ ID NO 36
```

```
<211> LENGTH: 24
<212> TYPE: DNA
<213> ORGANISM: Artificial Sequence
<220> FEATURE:
<223> OTHER INFORMATION: Primer

<400> SEQUENCE: 36
actagtcaat agcacaaatt gcca                                              24

<210> SEQ ID NO 37
<211> LENGTH: 24
<212> TYPE: DNA
<213> ORGANISM: Artificial Sequence
<220> FEATURE:
<223> OTHER INFORMATION: Primer

<400> SEQUENCE: 37
agccctagcc tatacatctt tcct                                              24

<210> SEQ ID NO 38
<211> LENGTH: 24
<212> TYPE: DNA
<213> ORGANISM: Artificial Sequence
<220> FEATURE:
<223> OTHER INFORMATION: Primer

<400> SEQUENCE: 38
aatgggcttt tccattcaat aata                                              24

<210> SEQ ID NO 39
<211> LENGTH: 24
<212> TYPE: DNA
<213> ORGANISM: Artificial Sequence
<220> FEATURE:
<223> OTHER INFORMATION: Primer

<400> SEQUENCE: 39
aaatgattgt tcgctgtatg ctaa                                              24

<210> SEQ ID NO 40
<211> LENGTH: 24
<212> TYPE: DNA
<213> ORGANISM: Artificial Sequence
<220> FEATURE:
<223> OTHER INFORMATION: Primer

<400> SEQUENCE: 40
atgtcatgtt tgattccatt tttg                                              24

<210> SEQ ID NO 41
<211> LENGTH: 24
<212> TYPE: DNA
<213> ORGANISM: Artificial Sequence
<220> FEATURE:
<223> OTHER INFORMATION: Primer

<400> SEQUENCE: 41
ctgctagaca tacttggaac atgg                                              24

<210> SEQ ID NO 42
<211> LENGTH: 24
<212> TYPE: DNA
<213> ORGANISM: Artificial Sequence
<220> FEATURE:
<223> OTHER INFORMATION: Primer

<400> SEQUENCE: 42
```

-continued

```
cagtcgaata atttagggag catt                                          24

<210> SEQ ID NO 43
<211> LENGTH: 24
<212> TYPE: DNA
<213> ORGANISM: Artificial Sequence
<220> FEATURE:
<223> OTHER INFORMATION: Primer

<400> SEQUENCE: 43
actgagtgat ggtagaaaag aggg                                          24

<210> SEQ ID NO 44
<211> LENGTH: 24
<212> TYPE: DNA
<213> ORGANISM: Artificial Sequence
<220> FEATURE:
<223> OTHER INFORMATION: Primer

<400> SEQUENCE: 44
cagaatttct cccatatata cgcc                                          24

<210> SEQ ID NO 45
<211> LENGTH: 24
<212> TYPE: DNA
<213> ORGANISM: Artificial Sequence
<220> FEATURE:
<223> OTHER INFORMATION: Primer

<400> SEQUENCE: 45
tcatctcttc aagactttcc tcct                                          24

<210> SEQ ID NO 46
<211> LENGTH: 24
<212> TYPE: DNA
<213> ORGANISM: Artificial Sequence
<220> FEATURE:
<223> OTHER INFORMATION: Primer

<400> SEQUENCE: 46
tttagtgtca cttcttcatc tcgc                                          24
```

EPICHLOË ENDOPHYTE

RELATED APPLICATIONS

This application is a U.S. National Phase application under 35 U.S.C. § 371 from International Patent Application No. PCT/IB2019/051304 filed Feb. 19, 2019, which claims the benefit of priority from New Zealand Patent Application No. 740056 filed on Feb. 21, 2018, and New Zealand Patent Application No. 743525 filed Jun. 15, 2018.

TECHNICAL FIELD

The present invention generally relates to an *Epichloë* endophyte that produces secondary metabolites having insecticidal activity in symbiotic association with a host plant, methods of using the endophyte to confer pest resistance on a host plant, and to combinations comprising the endophyte and a plant or part thereof, including seeds.

BACKGROUND OF THE INVENTION

Grown worldwide, cereal grasses are one of the oldest and most important crops. Cereal grasses are widely used to provide forage to livestock and grain to feed farmed animals, such as sheep, cows, pigs, and poultry.

*Secale cereale*, commonly known as Rye, is grown worldwide, typically for the production of grain. The grain is used primarily for making flour, bread and for direct consumption, particularly in those countries having a history of rye-bread consumption. The vegetative portions of *S. cereale* may be used as straw, or converted to silage, for use as animal fodder, including for in situ grazing.

Another important cereal grass is wheat. Wheat grain is used widely to produce the flour used in a large array of baked goods and for making pasta. Wheat is also used for the production of starch, malt, dextrose, gluten, alcohol and other commercial products. Vegetative portions of wheat plants may be used as straw, or converted to silage, or used for animal fodder, including for in situ grazing.

More cultivable land worldwide is used for wheat production than any other food crop with 2014 production estimates in the neighbourhood of 220 million hectares of wheat sown (UN Food and Agriculture Organization, 2014). Amongst the cereals, wheat production is second only to maize, with about 750 million tonnes of wheat produced in 2016 (UN Food and Agriculture Organization, 2016). Wheat has a protein content of about 13%, and is a leading source of human vegetal protein. Whole wheat is a source of essential nutrients and dietary fibre.

As would be expected from such widely grown agricultural crops, cereal grasses are targeted by many pests, the activities of which can severely reduce overall production. Known pests include, but are not limited to, many Lepidoptera (moths and butterflies) including pink borer and armyworms; aphids including cereal aphids (Homoptera); *thrips* (Thysanoptera); wireworms, ground beetle (*Zabrus tenebrioides*), cereal leaf beetles (*Oulema melanopus, O. gallaeciana*) and white grubs (Coleoptera); Diptera including leatherjackets (*Tipula* spp.), wheat bulb fly (*Delia coarctata*), leaf miners (*Agromyza* spp.), frit fly (*Oscinella frit*), Hessian fly (*Mayetiola destructor*), saddle gall midge (*Haplodiplosis marginata*); grasshoppers (Orthoptera); termites (Isoptera); nematodes and slugs.

To combat losses in productivity, effective pest protection during cultivation is required to ensure that a good quantity of acceptable quality grain is produced.

Known methods of pest control for cereal grasses include some or all of the following practices: the use of pest resistant cultivars, optimizing time of planting and planting with healthy seeds, effective crop rotation, destruction, and/or burial or removal of crop debris (stubble). Additional methods of pest control that may be required include the use of various pesticides on plants and/or seeds. At times, simultaneous application of two or more active substances may be required for the control of pests.

However, the use of many pesticides can be problematic due to the known problems associated with the chemicals frequently used for such purposes. Many pesticides are toxic and can be dangerous to human and animal consumers of treated agricultural crops (Casida and Quistad, 1998). In particular, the accumulation, in humans and animals of toxic pesticides can lead to serious health issues for individuals, particularly during early development. For example, pesticide exposure has been linked to respiratory disorders, developmental cancers and has been shown to have lasting effects on the development of mental abilities (Zejda et al. 1993). Many pesticides also kill beneficial organisms that help control pests and that carry out essential ecosystem services such as pollination and nutrient cycling.

The use of pesticides may be difficult to control in variable environmental conditions leading to unwanted dispersal of toxic compounds, for example by drift of sprays or by soil leaching. In addition, the pests may develop pesticide resistance for a number of reasons, including improper practice and handling, which can pose a real threat to crop (grain) yields. Accordingly there is a need for pest control measures that do not use applied pesticides.

It is an object of the present invention to provide at least one *Epichloë* endophyte strain which when combined with a host plant confers at least some level of pest protection and/or disease protection on the host plant without requiring the use of applied pesticides and/or to at least provide the public with a useful choice.

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

SUMMARY OF THE INVENTION

In a first aspect, the present invention relates to an isolated strain of *Epichloë* endophyte wherein the endophyte comprises a B10 allele size of 188±0.8 base pairs (bp) and a B11 allele size of 112±0.8 bp.

In another aspect, the invention relates to an isolated strain of *Epichloë* endophyte selected from the group consisting of AR3002 (NRRL 50579), AR3005 (NRRL 50580), AR3007 (NRRL #67556), and AR3042 (NRRL #67560) or combinations thereof.

In another aspect the invention relates to a combination comprising an isolated strain of *Epichloë* endophyte of the invention, and a host plant, wherein the combination produces at least one indole diterpene alkaloid or at least one ergot alkaloid.

In another aspect the invention relates to a host plant infected with an isolated strain of *Epichloë* endophyte of the invention.

In another aspect the invention relates to a method of making a stable host plant/*Epichloë* endophyte combination that produces at least one indole diterpene alkaloid or at least one ergot alkaloid comprising artificially infecting a host plant with an isolated strain of *Epichloë* endophyte of the invention, wherein the combination produces at least one indole diterpene alkaloid or at least one ergot alkaloid.

In another aspect the invention relates to a method of conferring at least some level of pest protection on a host plant comprising artificially infecting the host plant with an isolated strain of *Epichloë* endophyte of the invention to form a host plant/*Epichloë* endophyte combination, wherein the host plant/*Epichloë* endophyte combination produces at least one indole diterpene alkaloid or at least one ergot alkaloid.

In another aspect the invention relates to a plant seed infected with an isolated strain of *Epichloë* endophyte of the invention.

In another aspect the invention relates to the use of an isolated strain of *Epichloë* endophyte of the invention to produce at least one indole diterpene alkaloid or at least one ergot alkaloid.

In another aspect the invention relates to a method of deterring or reducing pest damage to the plants in an area of land comprising planting the area of land with a host plant infected with an *Epichloë* endophyte of the invention, a combination of the invention, or infected plant seed of the invention.

In another aspect the invention relates to a method of increasing the yield of a host plant comprising artificially infecting the host plant with an isolated strain of *Epichloë* endophyte of the invention to form a host plant/*Epichloë* endophyte combination, wherein the host plant/*Epichloë* endophyte combination produces a greater yield than a host plant that is not infected with the endophyte.

Other aspects of the invention may become apparent from the following description which is given by way of example only and with reference to the accompanying drawings.

The invention may also be said broadly to consist in the parts, elements and features referred to or indicated in the specification of application, individually or collectively, in any or all combinations of two or more of said parts, elements or features, and where specific integers are mentioned herein that have known equivalents in the art to which the invention relates, such known equivalents are deemed to be incorporated herein as if individually set forth.

BRIEF DESCRIPTION OF THE DRAWINGS

The invention will now be described by way of example only and with reference to the drawings in which.

DETAILED DESCRIPTION OF THE INVENTION

Definitions

Figure 1:
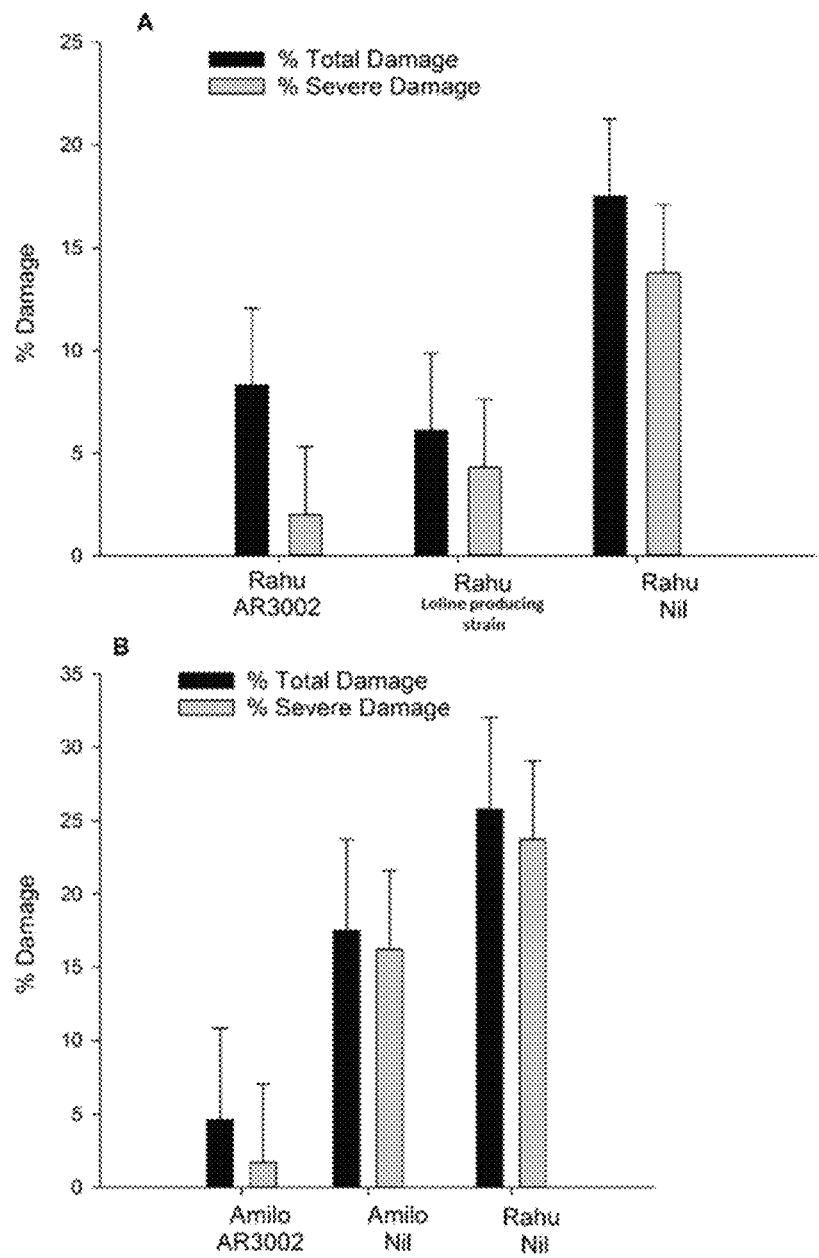
FIG. 1. Percentage of tillers with all levels of Argentine stem weevil (*Listronotus bonariensis*) larval damage (Total) and with moderate and severe damage (Severe) in *S. cereale* (rye or ryecorn) cultivar Rahu (A) and cultivar Amilo (B) infected with different endophyte strains or without endophyte (Nil). Error bars=SED.

The following definitions are presented to better define the present invention and as a guide for those of ordinary skill in the art in the practice of the present invention.

Unless otherwise specified, all technical and scientific terms used herein are to be understood as having the same meanings as is understood by one of ordinary skill in the relevant art to which this disclosure pertains. Examples of definitions of common terms in botany, microbiology, molecular biology and biochemistry can be found in Biology of Plants, Raven et al. (eds.), W.H. Freeman and Company, (2005); Plant Physiology, Taiz et al. (eds.), Sinauer Associates, Incorporated, (2010); Botany: An Introduction to Plant Biology, J. D. Mauseth, Jones & Bartlett Learning, (2003); Methods for General and Molecular Microbiology, 3rd Edition, C. A. Reddy, et al. (eds.), ASM Press, (2008); Encyclopedia of Microbiology, 2nd ed., Joshua Lederburg, (ed.), Academic Press, (2000); Microbiology By Cliffs Notes, I. Edward Alcamo, Wiley, (1996); Dictionary of Microbiology and Molecular Biology, Singleton et al. (2d ed.) (1994); Biology of Microorganisms $11^{th}$ ed., Brock et al., Pearson Prentice Hall, (2006); Biodiversity of Fungi: Inventory and Monitoring Methods, Mueller et al., Academic Press, (2004); Genes IX, Benjamin Lewin, Jones & Bartlett Publishing, (2007); The Encyclopedia of Molecular Biology, Kendrew et al. (eds.), Blackwell Science Ltd., (1994); Molecular Biology and Biotechnology: a Comprehensive Desk Reference, Robert A. Meyers (ed.), VCH. Publishers, Inc., (1995); Symbioses of grasses with seedborne fungal endophytes. Schardl C L et al. (2004) Annual Review of Plant Biology 55: 315-340; and Chemotype diversity of *Epichloë*, fungal symbionts of grasses, Schardl C L, Young C A, Faulkner J R, Florea S, Pan J (2012) Fungal Ecology 331-344 (Schardl et al., 2012).

It is also believed that practice of the present invention can be performed using standard botanical, microbiological, molecular biology and biochemistry protocols and procedures as known in the art, and as described, for example in Methods of Studying Root Systems, vol. 33, Wolfgang Böhm, Springer-Verlag, (1979); Root methods: A Handbook, Albert L. Smit Springer, (2000); Biodiversity of Fungi: Inventory and Monitoring Methods, Mueller et al., Academic Press, (2004); Environmental Microbiology: Methods and Protocols, J. F. T. Spencer et al., Humana Press, (2004); Environmental Microbiology, P. D. Sharma, Alpha Science International, (2005); Environmental Microbiology, J. R. Leadbetter, Gulf Professional Publishing, (2005), Molecular Cloning: A Laboratory Manual, Maniatis et al., Cold Spring Harbor Laboratory Press, (1982); Molecular Cloning: A Laboratory Manual (2 ed.), Sambrook et al., Cold Spring Harbor Laboratory Press, (1989); Guide to Molecular Cloning Techniques Vol. 152, S. L. Berger and A. R. Kimmerl (Eds.), Academic Press Inc., (1987); Biotechnology of Endophytic Fungi of Grasses. 1994 Bacon and White (Eds.), and other commonly available reference materials relevant in the art to which this disclosure pertains, and which are all incorporated by reference herein in their entireties.

The term "plant" as used herein encompasses whole plants and all parts of a plant from all stages of a plant life cycle including but not limited to vegetative and reproductive cells and tissues, propagules, seeds, embryos, shoots, stems, leaves, leaf sheaths and blades, inflorescences, roots, anthers, ligules, palisade, mesophyll, epidermis, auricles, palea, lemma and tillers.

The term "normal life cycle" as used herein refers to the normal reproductive cycle of a host plant, preferably a wheat or rye plant, preferably a hexaploid wheat plant, which includes growth of a first generation of plant to produce seeds which when germinated grow into a second generation of plant.

The term "normal phenotype" of a host plant as used herein refers to the typical morphology, growth and other phenotypic characteristics of the host plant as displayed during the life cycle of the host plant, including the host plant reproductive cycle and host plant seed as known and generally accepted in the art for that host plant when not containing endophyte.

The term "abnormal phenotype" referring to a host plant as used herein refers to the morphology, growth or other phenotypic characteristics of the host plant at any stage of the host plant life cycle including the host plant reproductive cycle and host plant seed which is different from that known and generally accepted in the art as typical or within the generally observed range for that host plant. The term "abnormal phenotype" referring to a host plant as used herein may include stunted plants or dwarf plants or plants with obvious visual external evidence of endophyte infection or plants failing to complete normal reproduction through seed, but is not limited thereto.

The term, "*Epichloë*" as used herein refers to *Epichloë* a genus of endophytic fungi comprising fungal endophytes from two previously named genera; the members of the anamorphic form genus *Neotyphodium* and the members of the teleomorphic genus *Epichloë* (Leuchtmann A, et al. 2014).

The term, "*Epichloë* endophyte" as used herein refers to an endophyte of the genus *Epichloë* that is known in the art, or that has been shown herein, to form a symbiotic association with a host plant.

The term, "conferring at least some level of pest protection" as used herein encompasses measurably reducing the incidence, severity and/or duration of the effects of a pest on a host plant as compared to a host plant lacking a fungal endophyte (a control plant), and/or a host plant having a different fungal endophyte. In some embodiments the host plant is a *Secale* spp. (rye) or *Triticum* spp. (wheat) plant, preferably *S. cereale* or *T. aestivum*, host plant that is infected with an *Epichloë* fungal endophyte according to the invention. Preferably a measureable reduction is a statistically significant reduction with a P-value of 0.05 or less.

The terms, "a level sufficient to confer pest protection" and "a level sufficient to confer pest resistance" and grammatical variations thereof as used herein with reference to levels of alkaloids mean any level of an alkaloid produced by the host plant-endophyte symbiosis that is sufficient to produce a measureable reduction in the incidence, severity or duration of a pest infestation, infection or detrimental effect on the host plant as compared to a host plant lacking a fungal endophyte (a control plant), and/or a host plant having a different fungal endophyte. In some embodiments the pest is an insect pest. In some embodiments the host plant is a *Secale* spp. (rye) or *Triticum* spp. (wheat) plant, preferably *S. cereale* or *T. aestivum*, host plant that is infected with an *Epichloë* fungal endophyte according to the invention. In some embodiments, the alkaloid is chanoclavine, paspaline or terpendole E. Preferably a measureable reduction is a statistically significant reduction with a P-value of 0.05 or less.

The term, "has increased resistance to plant disease" and grammatical variations thereof as used herein encompasses measurably reducing the incidence, severity and/or duration of the effects of a plant disease on a host plant as compared to a host plant lacking a fungal endophyte (a control plant), and/or a host plant having a different fungal endophyte. In some embodiments the host plant is a *Secale* spp. (rye) or *Triticum* spp. (wheat) plant, preferably *S. cereale* or *T. aestivum*, host plant that is infected with an *Epichloë* fungal endophyte according to the invention. Preferably a measureable reduction is a statistically significant reduction with a P-value of 0.05 or less.

The terms, "a level sufficient to confer protection from plant disease" and "a level sufficient to confer resistance to plant disease" and grammatical variations thereof as used herein with reference to levels of alkaloids mean any level of an alkaloid produced by the host plant-endophyte symbiosis that is sufficient to produce a measureable reduction in the incidence, severity or duration of a plant disease infestation, infection or detrimental effect on the host plant as compared to a host plant lacking a fungal endophyte (a control plant), and/or a host plant having a different fungal endophyte. In some embodiments the plant disease is a fungal disease. In some embodiments the host plant is a *Secale* spp. (rye) or *Triticum* spp. (wheat) plant, preferably *S. cereale* or *T. aestivum*, host plant that is infected with an *Epichloë* fungal endophyte according to the invention. In some embodiments, the alkaloid is chanoclavine, paspaline or terpendole E. Preferably a measureable reduction is a statistically significant reduction with a P-value of 0.05 or less.

The term "statistically significant" as used herein refers to the likelihood that a result or relationship is caused by something other than random chance. A result may be found to be statistically significant using statistical hypothesis testing as known and used in the art. Statistical hypothesis testing provides a "P-value" as known in the art, which represents the probability that the measured result is due to random chance alone. It is believed to be generally accepted in the art that levels of significance of 5% (0.05) or lower are considered to be statistically significant.

The term, "enhanced pest protection" as used herein refers to a level of pest protection conferred on a host plant in symbiotic association with an *Epichloë* fungal endophyte that reduces the incidence, severity and/or duration of a pest infestation, infection or detrimental effect on the plant due to the presence and/or activity of a given pest as compared to the incidence, severity and/or duration of the same pest infestation, infection and/or detrimental effect on a plant, preferably a grass plant, preferably a *Secale* spp. (rye) or *Triticum* spp. (wheat) plant, preferably *S. cereale* or *T. aestivum*, lacking a fungal endophyte (a control plant), and/or a host plant having a different fungal endophyte.

The terms, "artificially infecting" and "artificial inoculation" as used herein encompass any inoculation of a plant, particularly a plant, preferably a grass plant, preferably a *Secale* spp. (rye) or *Triticum* spp. (wheat) plant, preferably *S. cereale* or *T. aestivum*, preferably with AR3002, to form a plant/fungal symbiotic association that is not known from nature.

The term "non-endogenous" as used herein with reference to an endophyte in combination or in association with a host plant means that the endophyte is not found endogenously in the host plant; i.e., that the endophyte is a "non-endogenous" endophyte for that combination. Preferably the combination or association is a stable symbiotic combination or association. To be clear, a combination of a host plant and a non-endogenous endophyte as described herein is an artificial combination that is not found in nature. In some embodiments the host plant is a wheat plant, preferably wherein the wheat plant is a species, line or strain of hexaploid wheat, preferably *Triticum* spp., preferably *T. aestivum* or a variety or cultivar thereof.

The term "non-endogenous" as used herein with reference to a host plant in combination or in association with an *Epichloë* endophyte means that the host plant is not an endogenous host of the endophyte; i.e., that the host plant is a "non-endogenous" plant for that combination. Preferably the combination or association is a stable symbiotic combination or association. To be clear, a combination of a non-endogenous host plant and an *Epichloë* endophyte as described herein is an artificial combination that is not found in nature.

The term "in planta" as used herein in the context of fungal endophytes means a combination of an isolated strain of *Epichloë* endophyte of the invention and a host plant, wherein the endophyte is living symbiotically within the host plant, and preferably wherein the endophyte is in a stable plant/fungal symbiosis with the host plant.

The terms, "stable plant/fungal symbiosis" and "stable host plant/*Epichloë* endophyte combination as used herein refer to a symbiotic association that persists throughout the life cycle of the plant where the plant shows no external symptoms of endophyte infection. In a "stable host plant/*Epichloë* endophyte combination" the host plant is infected with the endophyte in a first generation and produces seeds which when germinated grow into a second generation of host plants that are also infected with the endophyte. Unless specifically stated otherwise, the term "combination" as used herein to refer to an isolated *Epichloë* endophyte and a host plant as described herein means a stable host plant/*Epichloë* endophyte combination.

The term "about" when used in connection with a referenced numeric indication means the referenced numeric indication plus or minus up to 10% of that referenced numeric indication. For example, "about 100" means from 90 to 110 and "about six" means from 5.4 to 6.6.

The term "base pairs" means canonical nucleic acid base pairs as known in the art.

The term, "AR3002 type" as used herein with reference to *Epichloë* fungal endophytes means endophytes, particularly AR3002, AR3005, AR3007 and, AR3042 that have the 22 identical SSR markers shown in Table 2.

The terms ans016, ans019, ans033, ans036, egs027, egs031, ces0004, ces0022, ces0041, ces0054, ces0060, ces0061, ces0067, ces0075, ces0076, ces0078, ces0089, ces0093, ces0094, and ces0095 as used herein specifically refer to the alleles having these labels as shown in Table 1.

The term "comprising" as used in this specification means "consisting at least in part of". When interpreting statements in this specification that include that term, the features, prefaced by that term in each statement, all need to be present but other features can also be present. Related terms such as "comprise" and "comprised" are to be interpreted in the same manner.

The term "consisting essentially of" as used herein means the specified materials or steps and those that do not materially affect the basic and novel characteristic(s) of the claimed invention.

The term "consisting of" as used herein means the specified materials or steps of the claimed invention, excluding any element, step, or ingredient not specified in the claim.

It is intended that reference to a range of numbers disclosed herein (for example, 1 to 10) also incorporates reference to all rational numbers within that range (for example, 1, 1.1, 2, 3, 3.9, 4, 5, 6, 6.5, 7, 8, 9 and 10) and also any range of rational numbers within that range (for example, 2 to 8, 1.5 to 5.5 and 3.1 to 4.7) and, therefore, all sub-ranges of all ranges expressly disclosed herein are hereby expressly disclosed. These are only examples of what is specifically intended and all possible combinations of numerical values between the lowest value and the highest value enumerated are to be considered to be expressly stated in this application in a similar manner.

DETAILED DESCRIPTION

Many cool-season grasses (Poaceae, subfam. Pooideae) possess seed-borne *Epichloë* fungal endophytes that are known for their bioprotective properties, and especially for production of anti-pest alkaloids such as lolines (Zhang et al., 2010) and peramine (Koulman et al., 2007). Asexual *Epichloë* (previously termed *Neotyphodium* species) are primarily or entirely transmitted vertically, whereas the sexual structures (stromata) of other related *Epichloë* species can give rise to horizontally transmissible spores (ascospores) (Zhang et al., 2010).

Symbiotic associations between *Epichloë* fungi and host grasses are common, and molecular phylogenetic evidence suggests that the species specificity observed in these symbiotic associations is due to the co-evolution of these groups of plants and fungal endophytes (Schardl et al., 2008).

Generally speaking, symbiotic associations formed between host plants and their *Epichloë* fungal endophytes are based on complex and intimate biological interactions which lead to a high degree of species specificity for both the endophyte and host (Simpson and Mace, 2012).

No modern domesticated cereals are naturally infected with *Epichloë* endophytes although some wild relatives may be (Marshall et al., 1999). Without wishing to be bound by theory, the inventors believe that during the evolution of modern cereals, agricultural practices such as storing seed may have led to the loss of historical associations if they existed (Welty et al., 1987).

Establishment of a stable plant/fungal symbiosis between an *Epichloë* endophyte and a host plant that is not a natural host for the fungus is both problematic and unpredictable (Simpson and Mace, 2012).

This is thought to be due to the requirement, in the formation of such symbioses, for successful integration of multiple biological variables between partners which can include ecological, biochemical and/or molecular incompatibilities (Christensen et al., 2000). The present disclosure details the large volume of research required, including significant trial and error experimentation, to develop successful protocols and procedures by which stable symbiotic associations between certain strains of *Epichloë* endophytes and cereal grass plants including wheat and rye, that are not the natural hosts for such fungal endophytes, have been established.

Surprisingly, the inventors have determined that artificial inoculation can be used to establish stable symbioses between some *Epichloë* endophytes and rye or wheat plants, particularly hexaploid wheat plants. Through the use of the inventive subject matter described herein, the inventors are able to produce infected host plants, particularly wheat and rye plants, that form stable symbiotic associations with the infecting fungal endophyte allowing the infected plant to progress through a normal life cycle, particularly that produce a tall floral phenotype that progresses through a normal life cycle including producing seed containing the endophyte that is able to germinate to form an infected next generation of the host plant.

Of note, modern wheat and rye cultivars do not naturally harbour *Epichloë* fungal endophytes. As the skilled artisan will appreciate *Epichloë* fungal endophytes are host specific and it is difficult to move *Epichloë* fungal endophytes between different host species.

Additionally, as a result of a lengthy research program, the applicants have identified *Epichloë* endophytes that produce in combination with a host plant (i.e., "in planta"), at least one indole diterpene alkaloid or at least one ergot alkaloid, as compared to an un-infected control plant. In one embodiment, the indole diterpene alkaloids may be paspaline, or terpendole E, and the ergot alkaloid may be chanoclavine.

Accordingly, in a first aspect, the present invention relates to an isolated strain of *Epichloë* endophyte wherein the endophyte comprises a B10 allele size of 188±0.8 base pairs (bp) and a B11 allele size of 112±0.8 bp.

In one embodiment the isolated strain of *Epichloë* endophyte comprises at least one additional SSR allele selected from the group consisting of ans016, ans019, ans033, ans036, egs027, egs031, ces0004, ces0022, ces0041, ces0054, ces0060, ces0061, ces0067, ces0075, ces0076, ces0078, ces0089, ces0093, ces0094, and ces0095, wherein the at least one additional SSR allele has the number of base pairs (bp) as shown in Table 2, ±0.8 bp.

In one embodiment the isolated strain of *Epichloë* endophyte comprises at least two additional SSR alleles, preferably at least 3, at least 4, at least 5, at least 6, at least 7, at least 8, at least 9, at least 10, at least 11, at least 12, at least 13, at least 14, at least 15, at least 16, at least 17, at least 18, at least 19 additional SSR alleles, preferably 20 additional SSR alleles, wherein each of the additional SSR alleles has the number of base pairs (bp) as shown in Table 2, ±0.8 bp.

In one embodiment the isolated strain of *Epichloë* endophyte comprises the following 22 SSR alleles: B10, B11, ans016, ans019, ans033, ans036, egs027, egs031, ces0004, ces0022, ces0041, ces0054, ces0060, ces0061, ces0067, ces0075, ces0076, ces0078, ces0089, ces0093, ces0094, and ces0095, wherein the 22 SSR alleles have the number of base pairs (bp) as shown in Table 2, ±0.8 bp.

In one embodiment the isolated strain of *Epichloë* endophyte produces in planta at least one indole diterpene alkaloid or at least one ergot alkaloid. In one embodiment the indole diterpene alkaloid is paspaline, or terpendole E. In one embodiment the ergot alkaloid is chanoclavine.

In one embodiment the isolated strain of *Epichloë* endophyte does not produce, in planta, more than about 0.1 mg/kg ergovaline or more than about 0.1 mg/kg lolitrem B or both, wherein mg/kg is by dry weight of the endophyte and the host plant infected with the endophyte.

In one embodiment the isolated *Epichloë* endophyte is isolated from a genus within the grass tribe Hordeeae (Triticeace). In one embodiment the isolated *Epichloë* endophyte is isolated from wild cereal grasses, preferably *Elymus* spp. grasses and/or *Hordeum* species grasses. In one embodiment the isolated *Epichloë* endophyte is isolated from *Elymus* spp., preferably *E. dahuricus, E. dahuricus* sub species *excelsus*, and/or *E. uralensis*.

In one embodiment the isolated *Epichloë* endophyte is a species or strain of *Epichloë bromicola* or a hybrid strain of *E. bromicola* and another *Epichloë* species.

In another aspect, the invention relates to an isolated strain of *Epichloë* endophyte selected from the group consisting of AR3002 (NRRL 50579), AR3005 (NRRL 50580), AR3007 (NRRL #67556), and AR3042 (NRRL #67569) or combinations thereof.

*Epichloë* endophyte strains described herein were isolated from *Elymus* spp. or *E. dahuricus* sourced from China and were deposited at The United States Department of Agriculture, Agricultural Research Service Midwest Area, National Center for Agricultural Utilization Research, 1815 North University Street, Peoria, Illinois, 61604-3902, USA on the following dates for strains:

AR3002 (NRRL 50579) on 13 Oct. 2011,
AR3005 (NRRL 50580) on 13 Oct. 2011,
AR3007 (NRRL #67556) on 5 Feb. 2018, and
AR3042 (NRRL #67560) on 5 Feb. 2018
according to the Budapest Treaty for purposes of patent procedure.

*Epichloë* endophytes strains as described herein were isolated from endophyte-infected plants following surface sterilisation of plant tissue as described by Christensen et al. 2002.

Once isolated, the isolated and/or biologically pure fungal endophyte may be cultured using standard techniques as known in the art and as disclosed herein, including in the examples.

In one embodiment, the *Epichloë* endophyte is cultured on antibiotic potato dextrose agar (ABPDA) between 20° C. and 25° C., preferably between 21° C. and 23° C. The optimal temperature for growth of the fungal endophyte is 22° C. Growth of the fungal endophyte at temperatures above or below this range may be possible although growth may be reduced or may cease entirely. In one embodiment, the fungal endophyte is cultured in the dark.

In one embodiment, the isolated strain of *Epichloë* endophyte comprises a B10 allele size of 188±0.8 base pairs (bp) and a B11 allele size of 112±0.8 bp.

In one embodiment the isolated strain of *Epichloë* endophyte comprises at least one additional SSR allele selected from the group consisting of ans016, ans019, ans033, ans036, egs027, egs031, ces0004, ces0022, ces0041, ces0054, ces0060, ces0061, ces0067, ces0075, ces0076, ces0078, ces0089, ces0093, ces0094, and ces0095, wherein the at least one additional SSR allele has the number of base pairs (bp) as shown in Table 2, ±0.8 bp.

In one embodiment the isolated strain of *Epichloë* endophyte comprises at least two additional SSR alleles, preferably at least 3, at least 4, at least 5, at least 6, at least 7, at least 8, at least 9, at least 10, at least 11, at least 12, at least 13, at least 14, at least 15, at least 16, at least 17, at least 18, at least 19 additional SSR alleles, preferably 20 additional SSR alleles, wherein each of the additional SSR alleles has the number of base pairs (bp) as shown in Table 2, ±0.8 bp.

In one embodiment the isolated strain of *Epichloë* endophyte comprises the following 22 SSR alleles: B10, B11, ans016, ans019, ans033, ans036, egs027, egs031, ces0004, ces0022, ces0041, ces0054, ces0060, ces0061, ces0067, ces0075, ces0076, ces0078, ces0089, ces0093, ces0094, and ces0095, wherein the 22 SSR alleles have the number of base pairs (bp) as shown in Table 2, ±0.8 bp.

In one embodiment the isolated strain of *Epichloë* endophyte produces in planta at least one indole diterpene alkaloid or at least one ergot alkaloid. In one embodiment the at least one indole diterpene alkaloid is paspaline, or terpendole E. In one embodiment the at least one ergot alkaloid is chanoclavine.

In one embodiment production in planta is in a non-endogenous plant host.

In one embodiment the isolated strain of *Epichloë* endophyte does not produce, in planta, more than about 0.1 mg/kg ergovaline or more than about 0.1 mg/kg lolitrem B or both, wherein mg/kg is by dry weight of the endophyte and the host plant infected with the endophyte.

In one embodiment the isolated *Epichloë* endophyte is isolated from a genus within the grass tribe Hordeeae (Triticeace). In one embodiment the isolated *Epichloë* endophyte is isolated from wild cereal grasses, preferably *Elymus* spp. grasses and/or *Hordeum* species grasses. In one embodiment the isolated *Epichloë* endophyte is isolated from *Elymus* spp., preferably *E. dahuricus, E. dahuricus* sub species *excelsus*, and/or *E. uralensis*.

In one embodiment the isolated *Epichloë* endophyte is a species or strain of *Epichloë bromicola* or a hybrid strain of *E. bromicola* and another *Epichloë* species.

In another aspect the invention relates to a combination comprising an isolated strain of *Epichloë* endophyte as described herein, and a host plant, wherein the combination produces at least indole diterpene alkaloid, or at least one ergot alkaloid.

In one embodiment the host plant is a non-endogenous host plant.

In some embodiments, inoculation into a host plant may be carried out using seedlings that have been germinated for about two weeks. Preferably the seedlings have been germinated for 4 to 9 days. In one embodiment the seedlings have been germinated for less than 4 days.

Outside of this range, seedlings may still form effective associations but in some cases may be too young or too old for establishment of the *Epichloë* endophyte. Seeds need to be free of non-target fungi and bacteria to ensure that the seedlings are not overcome by microbial contamination.

In one embodiment, artificial inoculation may be carried out using basal inoculation of host plant seedlings. To effectively establish the *Epichloë* symbiont/host plant association, inoculation of the endophyte should be made into the host plant meristem by incision of the plant and insertion of cultured fungal mycelium.

In one embodiment the host plant is a grass plant or part thereof, preferably a *Secale* spp. plant, preferably *S. cereale* or a cultivar thereof, preferably *S. cereale* cultivar Rahu or *S. cereale* cultivar Amilo. In one embodiment the grass plant is a wheat plant, preferably a *Triticum* spp. plant or a cultivar thereof, preferably a *T. aestivum* or cultivar thereof.

In one embodiment the part thereof of the host plant is a plant cell line or plant callus.

In one embodiment the at least one indole diterpene alkaloid is paspaline or terpendole E. In one embodiment the at least one ergot alkaloid is chanoclavine.

In one embodiment the combination has increased resistance to pests or increased resistance to plant disease or both, as compared to a host plant that is not infected with an *Epichloë* endophyte.

In one embodiment the combination has increased resistance to insect pests.

In one embodiment the host plant/endophyte combination has increased resistance to pests, wherein the pests are selected from the group consisting of: (1) species of aphids selected from the group consisting of *Rhopalosiphum padi, Schizaphis graminum, Rhopalosiphum maidis, Metopolophium dirhodum, Sitobion* spp., *Sitobion avenae, Sitobion fragariae*, and *Diuraphis noxia*; (2) species of grass and cereal flies selected from the group consisting of *Oscinella frit, Oscinella pusilla, Mayetiola destructor, Cerodontha* spp., *Cerodontha australis, Cerodontha angustipennis, Formia fumigata, Meromyze americana, Haplodiplosis marginata, Chlorops pumilionis, Tipula* spp. *Chromatomyia fuscula, Cephus pygmaeus, Chromatomyia fuscula*, and *Contarinia tritici*; (3) species of *thrips* selected from the group consisting of *Limothrips cerealium, Limothrips denticornis, Aptinothrips rufus*, and *Stenothrips graminum*; (4) species of grasshoppers and crickets selected from the group consisting of *Locusta migratoria, Phaulacridium marginate, Phaulacridium vittatum, Melanoplus* spp., and *Teleogryllus commodus*; (5) species of bugs *Nysius huttoni* or *Blissus leucopertus leucopertus*; (6) weevils of *Sphenophorus* spp. or *Listronotus* spp., including *Listronotus bonariensis* (Argentine stem weevil); (7) species of armyworm, cutworm and leafrollers selected from the group consisting of *Pseudaletia unipuncta, Spodoptera* spp., *Mythimna separata; Persectania aversa, Agrotis ipsilon*, and *Epiphyas postvittana*; (8) *Oulema melanopus* leaf bugs; (9) species of white grubs selected from the group consisting of *Popillia japonica, Costelytra giveni* (formerly *C. zealandica*), *Phyllopertha* spp., *Rhizotrogus majalis*, and *Anisoplia segetum*; (10) species of mealybug selected from the group consisting of *Phenacoccus hordei, Balanococcus poae, Ripersella rumicis*, and *Porphyrophora tritici*; (11) species of wireworms *Conoderus* spp., or *Limonius* spp.; (12) *Zabrus tenebrioides* beetles; (13) species of mites selected from the group consisting of *Penthaleus* spp., *Halotydeus destructor*, and *Aceria* spp.; (14) species of stored product pests selected from the group consisting of *Sitophilus oryzae, Sitophilus granarius, Sitotroga cerealella, Rhyzopertha dominica, Cryptolestes* spp., *Oryzaephilus surinamensis, Cadra cautella, Plodia interpunctella, Tribolium confusum, Tribolium castaneum*, and *Lasioderma erricorne*; (15) *Philaenus spumarius* froghoppers; (16) species of nematodes selected from the group consisting of root lesion nematodes of *Pratylenchus* spp. selected from the group consisting of *P. thornei, P. crenatus, P. neglectus* and *P. penetrans*, cereal cyst nematodes of *Heterodera* spp. and *Punctodera* spp. selected from the group consisting of *H. avenae, H latipons, H. hordecalis, H. filipjevi, H. mani, H. bifenestra, H. pakistanensis* and *P. punctata*, root knot nematodes of *Meloidogyne* spp. selected from the group consisting of *M. chitwoodi, M. naasi, M. artiellia, M. microtyla, M. ottersoni, M. graminicola, M. graminis, M. kikuyensis* and *M. spartinae*, stem nematodes of *Ditylenchus* spp. selected from the group consisting of *D. dipsicai* and *D. radicicola*; and the seed gall nematode *Anguina tritici*; (17) species of slugs selected from the group consisting of *Deroceras reticulatum, Arion hortensis* agg. and *A. subfuscus*

In one embodiment the pests are weevils, preferably Argentine stem weevils (ASW) (*Listronotus bonariensis*). In one embodiment the pests are *Cerodontha australis*.

In one embodiment the pests are nematodes, preferably root lesion nematodes (*Pratylenchus* spp.).

In one embodiment the host plant/endophyte combination has increased resistance to plant disease, wherein the plant disease is caused by a plant pathogen selected from the group consisting of Barley yellow dwarf virus (Leteovirus), wheat soil-borne mosaic virus (Furovirus) and wheat streak mosaic virus (Tritimovirus), *Xanthomonas campestris, Pseudomonas syringae, Colletotrichum graminicola, Glomerella graminicola* [teleomorph], *Alternaria* spp., *Cladosporium herbarum, Mycosphaerella tassiana* [teleomorph], *Epicoccum* spp., *Sporobolomyces* spp., *Stemphylium* spp., *Bipolaris sorokiniana, Cochliobolus sativus* [teleomorph], *Fusarium* spp., *Tilletia caries, Tilletia tritici, Tilletia laevis, Tilletia foetida, Hymenula cerealis, Cephalosporium gramineum, Helminthosporium sativum, Cochliobolus sativus* [teleomorph], *Coprinus sychromorbidus, Dilophospora alopecuri, Tilletia controversa, Claviceps purpurea, Sphacelia segetum* [anamorph], *Fusarium culmorum, Pseudoseptoria donacis, Selenophoma donacis, Neovossia indica, Tilletia indica, Puccinia recondita, Aecidium clematidis* [anamorph], *Cercosporidium graminis, Scolicotrichum graminis, Phaeosphaeria herpotrichoides, Leptosphaeria herpotrichoides, Ustilago tritici, Microdochiurn nivale, Fusarium nivale, Monographella nivalis* [teleomorph], *Erysiphe graminis, Pythium aphanidermatum, Pythium arrhenomanes, Pythium debaryanum, Pythium graminicola, Pythium ultimum, Gibberella zeae, Fusarium graminearum*

[anamorph], *Septoria secalis, Septoria tritici, Mycosphaerella graminicola* [teleomorph], *Rhizoctonia cerealis, Rhizoctonia solani, Rhizoctonia zeae, Blumeria* spp., *Ceratobasidium cereale* [teleomorph], *Myrosclerotinia borealis, Sclerotinia borealis, Typhula idahoensis, Typhula incarnate, Typhula ishikariensis, Typhula ishikariensis* var. *canadensis, Stagonospora nodorum, Septoria nodorum, Phaeosphaeria nodorum* [teleomorph], *Leptosphaeria nodorum, Urocystis occulta, Puccinia graminis, Aspergillus* spp., *Nigrospora* spp., *Penicillium* spp., *Rhizopus* spp., *Pseudocercosporella herpotrichoides, Tapesia acuformis* [teleomorph], *Uredo glumarum* [anamorph], *Pyrenophora tritici-repentis, Drechslera tritici-repentis* [anamorph], *Helminthosporium tritici-repentis, Puccinia triticina, Pythium* spp., *Rhynchosporium secalis, Puccinia striiformis, Gaeumannomyces graminis, Magnaporthe oryzae* and *Fusarium pseudograminearum*.

Preferably the plant pathogen is *Puccinia recondita, Puccinia triticina, Puccinia graminis, Fusarium* spp., *Pythium* spp., *Rhynchosporium secalis, Puccinia striiformis, Gaeumannomyces graminis*, or *Fusarium pseudograminearum*.

In one embodiment the isolated *Epichloë* endophyte in the combination is a non-endogenous endophyte.

In some embodiments the isolated strain of *Epichloë* endophyte is as set out for any other aspect of this invention, including but not limited to SSR alleles, SSR allele sizes, isolated strains deposited under the Budapest Treaty, production of alkaloids, particularly indole diterpene alkaloids and ergot alkaloids, the original plant host from which the endophyte was isolated, isolation conditions, culture conditions, inoculation conditions, enhanced pest protection, and the production or non-production of ergovaline and/or Lolitrem B.

In another aspect the invention relates to a host plant infected with an isolated strain of *Epichloë* endophyte wherein the endophyte comprises a B10 allele size of 188±0.8 bp and a B11 allele size of 112±0.8 bp. In one embodiment the host plant is a non-endogenous host plant. In one embodiment the endophyte is a non-endogenous endophyte.

Contemplated herein as specific embodiments of this aspect of the invention relating to a host plant infected with an *Epichloë* endophyte are all of the embodiments set out above relating to the previous aspects of the invention including the specific embodiments set forth relating to isolated strains of *Epichloë* endophytes, host plants, pests, and combinations comprising an isolated strain of *Epichloë* endophyte and a host plant.

In another aspect the invention relates to a method of making a stable host plant/*Epichloë* endophyte combination that produces at least one indole diterpene alkaloid or at least one ergot alkaloid comprising artificially infecting a host plant with an isolated strain of *Epichloë* endophyte according to the invention, wherein the combination produces at least one indole diterpene alkaloid or at least one ergot alkaloid.

In one embodiment the host plant is a non-endogenous host plant.

In one embodiment the endophyte is a non-endogenous endophyte.

In some embodiments, the method further comprises propagating the host plant/*Epichloë* endophyte combination.

In some embodiments, the method further comprises obtaining seed from the propagated combination.

In some embodiments, the method further comprises identifying the presence of the endophyte in the seed.

In some embodiments, the method further comprises metabolic profiling of the host plant/*Epichloë* combination.

Metabolic profiling of a host plant/*Epichloë* combination, particularly to identify alkaloids that are produced in the combination, is believed to be within the skill of those in the art in view of the disclosure of the present specification and common general knowledge.

In some embodiments, the method further comprises selecting a host plant/*Epichloë* combination that produces at least one indole diterpene alkaloid or at least one ergot alkaloid. In one embodiment the at least one indole diterpene alkaloid is paspaline or terpendole E. In one embodiment the at least one ergot alkaloid is chanoclavine.

Contemplated herein as specific embodiments of this aspect of the invention relating to a method of making a stable host plant/*Epichloë* endophyte combination are all of the embodiments set out above relating to the previous aspects of the invention including the specific embodiments set forth relating to isolated strains of *Epichloë* endophytes, host plants, combinations comprising an isolated strain of *Epichloë* endophyte and a host plant, and host plants infected with an isolated strain of *Epichloë* endophyte.

In another aspect the invention relates to a method of conferring at least some level of pest protection on a host plant comprising artificially infecting the host plant with an isolated strain of *Epichloë* endophyte of the invention to form a host plant/*Epichloë* endophyte combination, wherein the host plant/*Epichloë* endophyte combination produces at least one indole diterpene alkaloid or at least one ergot alkaloid.

In one embodiment the at least one indole diterpene alkaloid or at least one ergot alkaloid confers the level of pest protection. In one embodiment the at least one indole diterpene alkaloid is paspaline or terpendole E. In one embodiment the at least one ergot alkaloid is chanoclavine.

In one embodiment the level of pest protection reduces pest damage to the host plant/*Epichloë* endophyte combination by at least 0.5%, preferably by at least 1%, by at least 5%, by at least 10%, by at least 20%, by at least 30%, by at least 40%, by at least 50%, by at least 60%, by at least 70%, by at least 80%, by at least 90%, by at least 95%, preferably by at least 99% as compared to the same species of host plant that is not infected with the *Epichloë* endophyte.

Contemplated herein as specific embodiments of this aspect of the invention relating to a method of conferring at least some level of pest protection on a host plant are all of the embodiments set out above relating to the previous aspects of the invention including the specific embodiments set forth relating to isolated strains of *Epichloë* endophytes, host plants, pests, combinations comprising an isolated strain of *Epichloë* endophyte and a host plant, host plants infected with an isolated strain of *Epichloë* endophyte, and methods of making a stable host plant/*Epichloë* endophyte combination.

In another aspect the invention relates to a plant seed infected with an isolated strain of *Epichloë* endophyte as described herein.

In one embodiment the plant seed is a seed of a *Secale* spp., preferably a seed of *Secale cereale* or a cultivar thereof, preferably a seed of *S. cereale* cultivar Rahu or *S. cereale* cultivar Amilo. In one embodiment the grass seed is the seed of a wheat plant, preferably a seed of a *Triticum* spp. or a cultivar thereof, preferably a seed of *T. aestivum* or cultivar thereof.

In some embodiments the isolated strain of *Epichloë* endophyte is as set out for any other aspect of this invention, including but not limited to SSR alleles, SSR allele sizes, isolated strains deposited under the Budapest Treaty, production of alkaloids, particularly indole diterpene alkaloids and ergot alkaloids, the original plant host from which the endophyte was isolated, isolation conditions, culture conditions, inoculation conditions, enhanced pest protection, and the production or non-production of ergovaline and/or Lolitrem B.

In another aspect the invention relates to the use of an isolated strain of *Epichloë* endophyte as described herein to produce at least one indole diterpene alkaloid or at least one ergot alkaloid.

In one embodiment the use comprises or consists essentially of artificially infecting a host plant with the isolated strain of *Epichloë* endophyte.

Contemplated herein as specific embodiments of this aspect of the invention relating to the use of an isolated strain of *Epichloë* endophyte are all of the embodiments set out above relating to the previous aspects of the invention including the specific embodiments set forth relating to isolated strains of *Epichloë* endophytes, host plants, pests, combinations comprising an isolated strain of *Epichloë* endophyte and a host plant, host plants infected with an isolated strain of *Epichloë* endophyte, methods of making a stable host plant/*Epichloë* endophyte combination and plant seeds infected with an isolated strain of *Epichloë* endophyte.

In another aspect the invention relates to a method of deterring or reducing pest damage to the plants in an area of land comprising planting the area of land with a host plant infected with an *Epichloë* endophyte of the invention, a combination of the invention, or infected plant seed of the invention.

In one embodiment the pest damage is insect pest damage.

In one embodiment the area of land is a pre-determined area of land on which deterrence or reduction of pest damage is desired. In one embodiment the area of land, or pre-determined area of land is a verge, divider, clearing, field, meadow, pasture or paddock.

In one embodiment the area of land is used in agriculture.

In one embodiment, at least 10%, preferably at least 20%, at least 30%, at least 40%, at least 50%, at least 60%, at least 70%, at least 80%, at least 90%, at least 95%, preferably about 99%, preferably all of the area of land is planted.

In one embodiment pest damage is reduced by at least 1%, preferably by at least 5%, at least 10%, at least 20%, at least 30%, at least 40%, at least 50%, at least 60%, at least 70%, at least 80%, at least 90%, at least 95%, preferably at least 99% as compared to an area of land that is the same size, but that has not been planted with a host plant infected with the *Epichloë* endophyte, the combination or the infected plant seed.

Contemplated herein as specific embodiments of this aspect of the invention relating to a method of deterring or reducing insect herbivory in an area of land are all of the embodiments set out above relating to the previous aspects of the invention including the specific embodiments set forth relating to isolated strains of *Epichloë* endophytes, host plants, pests, combinations comprising an isolated strain of *Epichloë* endophyte and a host plant, host plants infected with an isolated strain of *Epichloë* endophyte, methods of making a stable host plant/*Epichloë* endophyte combination, plant seeds infected with an isolated strain of *Epichloë* endophyte and the use of an isolated strain of *Epichloë* endophyte.

In another aspect the invention relates to a method of increasing the yield of a host plant comprising artificially infecting the host plant with an isolated strain of *Epichloë* endophyte of the invention to form a host plant/*Epichloë* endophyte combination, wherein the host plant/*Epichloë* endophyte combination produces a greater yield than a host plant that is not infected with the endophyte.

In one embodiment the yield is forage yield. In one embodiment the forage yield is whole crop cereal silage. In one embodiment the forage yield is total yield.

In one embodiment the forage yield is increased by about 0.5%, preferably by about 1%, by about 5%, by about 10%, by about 20%, by about 30%, by about 40%, preferably by about 50%.

In one embodiment the forage yield is increased by at least 0.5%, preferably by at least 1%, at least 5%, at least 10%, at least 20%, at least 30%, at least 40%, preferably by at least 50%.

In one embodiment the yield is grain yield.

In one embodiment grain yield is increased by about 0.5% to about 50%, preferably by about 1% to about 45%, about 5% to about 40%, about 10% to about 40%, about 15% to about 40%, about 20% to about 40%, about 20% to about 30%, preferably about 20% to about 25%, preferably about 46%, preferably about 23%.

In one embodiment the grain yield is increased by at least 0.5%, preferably by at least 1%, at least 5%, at least 10%, at least 20%, at least 30%, preferably by at least 40%. In one embodiment grain yield is increased by at least 20%, preferably at least 21%, preferably at least 22%. In one embodiment grain yield is increased by at least 40%, preferably by at least 45%.

In one embodiment the yield is straw yield.

In one embodiment the straw yield is increased by about 0.5%, preferably by about 1%, by about 5%, by about 10%, by about 20%, by about 30%, by about 40%, preferably by about 50%, about 54%, about 55%, preferably about 56%.

In one embodiment the straw yield is increased by at least 0.5%, preferably by at least 1%, at least 5%, at least 10%, at least 20%, at least 30%, at least 40%, by at least 50%, by at least 54%, by at least 55%, preferably by at least 56%.

Contemplated herein as specific embodiments of this aspect of the invention relating to a method of increasing the yield of a host plant are all of the embodiments set out above relating to the previous aspects of the invention including the specific embodiments set forth relating to isolated strains of *Epichloë* endophytes, host plants, pests, combinations comprising an isolated strain of *Epichloë* endophyte and a host plant, host plants infected with an isolated strain of *Epichloë* endophyte, methods of making a stable host plant/*Epichloë* endophyte combination, plant seeds infected with an isolated strain of *Epichloë* endophyte, the use of an isolated strain of *Epichloë* endophyte, and a method of deterring or reducing insect herbivory in an area of land.

Contemplated herein as specific embodiments of all aspects of the invention set forth above are embodiments in which the endophyte is a non-endogenous endophyte.

Contemplated herein as specific embodiments of all aspects of the invention set forth above are embodiments in which the host plant is a non-endogenous host plant.

Various aspects of the invention will now be illustrated in non-limiting ways by reference to the following examples.

EXAMPLES

Example 1

Detection of Fungal Endophyte Strains

In excess of 580 accessions of seed of *Elymus* spp. were obtained from various sources and, where numbers of seed allowed, up to approximately 50 individual seed or seedlings were examined for infection with endophyte. Live endophyte in leaf sheaths of seedlings grown to the stage of two or more tillers was determined by the method of Simpson et al. (2012). Approximately 6% of accessions were shown to produce at least one seedling containing live endophyte which could be further examined as part of the following examples.

Example 2

Detection of Genetic Variation of Fungal Endophyte Strains

Endophyte strains AR3002, AR3005, AR3007 and AR3042 were characterised and distinguished for genetic variation by DNA 'fingerprinting' based on genotypic data derived from up to 22 selected simple sequence repeat (SSR) marker loci using primer sequences of Table 1. These primer sequences had previously been shown to generally amplify *Epichloë* endophyte polymorphic DNA sequences from when the endophytes are in planta (Moon et al. 1999; Kirkby et al, 2011; Simpson et al. 2012; Card et al, 2014.)

Samples of about 100 mg fresh weight of basal tiller were used to extract total genomic DNA (plant+endophyte), following the plant DNA isolation procedure of the FastDNA kit as recommended by the manufacturer (MP Biomedicals, Solon, Ohio, USA) for plant samples.

SSR amplification was conducted with oligonucleotide primer pairs, using one of two polymerase chain reaction (PCR) protocols (Table 1). In both protocols PCR was carried out using an iCycler thermocycler (BioRad, Hercules, California, USA).

Protocol 1 was as described by Moon (Moon et al., 1999), except that an annealing temperature of 60° C. was used. In this protocol forward primers were labelled at the 5' terminus with the fluorophore 6-FAM™ (Applied Biosystems, Foster City, California, USA).

In Protocol 2 forward primers were synthesised with a 21 nucleotide M13 tail sequence at the 5'-terminus (5'-TGTAAAACGACGGCCAGT-3') (SEQ ID NO: 1), to facilitate universal labelling of PCR products by a 6-FAM™-labelled M13 primer (Schuelke, 2000). Reverse primers were synthesised with the sequence 5'-GTTTCTT-3' (SEQ ID NO: 2) at the 5'-terminus end to promote non-templated adenylation at the 3'-terminus end of PCR product (Brownstein et al., 1996). A 10 µL PCR reaction volume was used, containing approximately 10 ng of total genomic DNA, 2.5 mM magnesium chloride, 1x PCR buffer, 0.05 mM of each dNTP, 0.0375 µM forward primer, 0.15 µM reverse primer, 0.15 µM of fluorescent-labelled M13 primer and 0.75 U of Platinum Taq DNA polymerase (Invitrogen, Carlsbad, California). PCR was carried out using the following profile: (1) 94° C. for 4:00 minutes, (2) 30 cycles of: 94° C. for 30 seconds, 55° C. for 30 seconds and 72° C. for 30 seconds, (3) 8 cycles of: 94° C. for 30 seconds, 53° C. for 30 seconds and 72° C. for 30 seconds, (4) 72° C. for 30 minutes (after Schuelke 2000).

PCR products were analysed by capillary electrophoresis on an ABI 3130xl Genetic Analyser using a 22 cm capillary array with POP-7™ polymer (Applied Biosystems). GS500 LIZ (Applied Biosystems) was used as an internal size standard. Electropherograms were analysed using ABI Prism GeneScan (v 3.7, Applied Biosystems), and genotype data was scored using Genemarker analysis software (SoftGenetics LLC, Pennsylvania, USA).

The inventors note here that in their experience, allele sizes will vary in some analyses according to a number of factors. For example, estimates of fragment (allele) sizes based on capillary electrophoresis are affected by factors including, but not limited to, the type of instrument, the length of the capillary array, the type of polymer used and environmental variables including ambient temperature. Accordingly, the SSR allele sizes in bp that are reported herein, including those in Table 2 below, are associated with the analysis platform described and also include a confidence interval of ±0.8 bp.

Plants examined above were then further characterised by performing chemical analyses. Six infected seedlings were further examined for the presence of alkaloids, attributable to the presence of endophytes, such as indole diterpenes, ergot alkaloids, peramine and lolines.

TABLE 1

SSR primer sequences.

| SSR | | Primer sequences (5'-3') | PCR protocol | SEQ ID NO: |
|---|---|---|---|---|
| B10 | forward | CGCTCAGGGCTACATACACCATGG | 1 | 3 |
| | reverse | CTCATCGAGTAACGCAGGCGACG | | 4 |
| B11 | forward | CATGGATGGACAAGAGATTGCACG | 1 | 5 |
| | reverse | TTCACTGCTACAATTCTGTCCAGC | | 6 |
| ans016 | forward | CACAAAGACAAACGCCAAAAG | 2 | 7 |
| | reverse | GCAAAGCTCACAGACAAAGGTC | | 8 |
| ans019 | forward | TACCTCTGCACGGTGTATTCC | 2 | 9 |
| | reverse | TGCATAACACTCACCTTATAGTCG | | 10 |
| ans033 | forward | GCGTTGAGGAGGCTAGATAGAA | 2 | 11 |
| | reverse | TTCCAAGCTGAACAAAAGTCAA | | 12 |
| ans036 | forward | ATTTGCAGCAGAGATGATGTGT | 2 | 13 |
| | reverse | CCTGCACCGGACTGTTAGTAAT | | 14 |
| egs027 | forward | GATGACGTATCTTGATGCTACCAC | 2 | 15 |
| | reverse | CGTGTATAAAGTTCGGGATCCTAT | | 16 |
| egs031 | forward | GAGATATCCCGTCTCCTGATCTAA | 2 | 17 |
| | reverse | CACAGCGTTACACTATCAACTTCC | | 18 |

TABLE 1-continued

SSR primer sequences.

| SSR | | Primer sequences (5'-3') | PCR protocol | SEQ ID NO: |
|---|---|---|---|---|
| ces0004 | forward | CACTAAACACACCCAAGAACAAGA | 2 | 19 |
| | reverse | AGACAGGTAAGAAGTTTTCCCCTT | | 20 |
| ces0022 | forward | AGCTTTCCAATGACGACATACATA | 2 | 21 |
| | reverse | TAATTTAGGGTAGCATTTTCTCCG | | 22 |
| ces0041 | forward | GGTCCCTATTCTAATGCAGGTATG | 2 | 23 |
| | reverse | CAGTGTACGGGACTTTGTCAATAC | | 24 |
| ces0054 | forward | TGTATAATAAACATGGCGTGCTCT | 2 | 25 |
| | reverse | GTGTTGAAAGTTGTTGGATCACTC | | 26 |
| ces0060 | forward | CGAAATTGTAGACTATGTTGGAGC | 2 | 27 |
| | reverse | GTAGATGTATTTTGAGCAGGGCTT | | 28 |
| ces0061 | forward | GAGTGAGACCCGGTGTAGTAAGTC | 2 | 29 |
| | reverse | GAGTCATTCTTCGTCCATTGTCTT | | 30 |
| ces0067 | forward | GAAATGAGGCGTCTATCTTAAAGC | 2 | 31 |
| | reverse | TTTCTTGATTTCCAAAGAACAACA | | 32 |
| ces0075 | forward | CAGTCATCGATTAAAAGTGAGCAT | 2 | 33 |
| | reverse | ATGTCATCTGCTTCAACAAGAGTC | | 34 |
| ces0076 | forward | TCTTCCATACAATTTCTTCCCTTC | 2 | 35 |
| | reverse | ACTAGTCAATAGCACAAATTGCCA | | 36 |
| ces0078 | forward | AGCCCTAGCCTATACATCTTTCCT | 2 | 37 |
| | reverse | AATGGGCTTTTCCATTCAATAATA | | 38 |
| ces0089 | forward | AAATGATTGTTCGCTGTATGCTAA | 2 | 39 |
| | reverse | ATGTCATGTTTGATTCCATTTTTG | | 40 |
| ces0093 | forward | CTGCTAGACATACTTGGAACATGG | 2 | 41 |
| | reverse | CAGTCGAATAATTTAGGGAGCATT | | 42 |
| ces0094 | forward | ACTGAGTGATGGTAGAAAAGAGGG | 2 | 43 |
| | reverse | CAGAATTTCTCCCATATATACGCC | | 44 |
| ces0095 | forward | TCATCTCTTCAAGACTTTCCTCCT | 2 | 45 |
| | reverse | TTTAGTGTCACTTCTTCATCTCGC | | 46 |

TABLE 2

SSR allele sizes for strains AR3002, AR3005, AR3007 and AR3042 in base pairs (bp) ± 0.8.

| SSR | Allele size |
|---|---|
| B10 | 188 |
| B11 | 112 |
| ans016 | 282 |
| ans019 | 204 |
| ans033 | 181 |
| ans036 | 286 |
| egs027 | 359 |
| egs031 | 259 |
| ces0004 | 185 |
| ces0022 | 209 |
| ces0041 | 261 |
| ces0054 | 261 |
| ces0060 | 238 |
| ces0061 | 162 |
| ces0067 | 277 |
| ces0075 | 243 |
| ces0076 | 157 |
| ces0078 | 310 |
| ces0089 | 165 |
| ces0093 | 145 |
| ces0094 | 329 |
| ces0095 | 360 |

Example 3

Isolation of Fungal Endophyte Strains

AR3002, AR3005, AR3007 and AR3042 were isolated from endophyte-infected *Elymus* spp. plants, including *E. dahuricus* plants following surface sterilisation of plant tissue as generally known in the art, particularly as described by Christensen et al. (2002). Tillers were removed from plants by cutting at the base and trimming to about 5 cm before surface sterilising. Sectioned tillers were surface sterilised by quick rinse with 96% ethanol and a 1 minute soak in a 10% bleach solution followed by rinsing twice in sterile water. Tillers were sectioned transversely; sheath rings were separated and placed on to 5 μg/ml tetracycline antibiotic potato dextrose agar (ABPDA). The Petri plates were incubated in the dark at 22-25° C. for 3-5 weeks. Cultures could be sub-cultured on the same medium.

Cultures were examined for colony growth rates, colony morphology, ability to produce conidia, size range of conidia, SSR allele sizes, and other descriptive features (Table 3).

The selection of AR3002, AR3005, AR3007 and AR3042 for further examination was based on its genotype and secondary metabolite profile.

AR3002, AR3005, AR3007 and AR3042 cultures prepared and sometimes sub-cultured in the manner of this example were used for testing the inoculation and possible enduring infection of *Secale cereale* seedlings as described below.

Example 4

Endophyte Descriptions

In vitro characteristics when grown on PDA were consistent with descriptions of *Neotyphodium* (Christensen et al., 1993; Glenn et al., 1996), being slow to moderately slow growing, ranging after 4 weeks on PDA. Colonies raised from the agar, white, cottony, slightly to strongly convoluted, felty, with abundant aerial hyphae. Colony reverse tan to cream at margin. Conidiogenous cells were solitary, arising perpendicularly from the hyphae, wider at the base and tapering at the tip. Phialidic conidia were hyaline, smooth, navicular to lunate, 2.05-14.96 μm long×1.37-8.19 μm wide. None of the isolates were sterile. Individual characteristics per strain are listed in table 3.

TABLE 3

Conidial and colony dimensions

| Host | Endophyte | Conidia (μm) | | | | | | Colony | |
| --- | --- | --- | --- | --- | --- | --- | --- | --- | --- |
| | | Av. length | Av. width | Min Length | Max Length | Min width | Max width | Colony diameter (mm) | STDEV |
| *Elymus dahuricus* | AR 3002 | 4.64 × | 2.36 | 2.92 | 5.68 | 1.70 | 3.30 | 20.7 | 0.7 |
| *Elymus* sp. | AR 3005 | 4.30 × | 2.49 | 3.59 | 5.41 | 2.05 | 3.18 | 24.0 | 2.7 |
| | AR 3007 | 4.71 × | 2.24 | 3.21 | 6.07 | 1.53 | 2.93 | 22.5 | 1.0 |
| | AR 3042 | 4.81 × | 2.54 | 3.30 | 7.00 | 1.90 | 3.44 | 32.0 | 2.6 |

Example 5

Inoculation of *Epichloë* Fungal Endophytes into *Secale cereale*

Seeds of *Secale cereale*, cultivars Rahu and Amilo, were surface sterilised and inoculated with an isolated *Epichloë* endophyte as described herein using methodology as described by Latch and Christensen (1985). Seeds were surface sterilised by immersion in a 50% sulphuric acid solution for 15 minutes followed by a five times rinse with tap water and immersion in a 10% domestic bleach (Janola) solution for 15 minutes followed by two rinses in sterile water. Seeds were dried in a laminar flow cabinet on sterile Whatmann filter paper before arranging on 4% water agar Petri plates. The seeds on plates were germinated in the dark at 22-25° C. for 4-9 days and resulting etiolated seedlings were inoculated before being returned to the dark incubator for 7 days. Following this incubation plates were placed under white fluorescent lights for at least 7 days before removing seedlings and planting them in commercial potting mix and growing them in a glasshouse. Plants were grown for ca. 6 weeks before identifying infected individuals. Infected plants were identified by the method of Simpson et al. (2012). Plants were further grown in a glasshouse to examine the plant phenotype of infected plants in comparison with the typical uninfected plants and in particular to determine whether inflorescences and seed heads would be formed.

Figure 2:
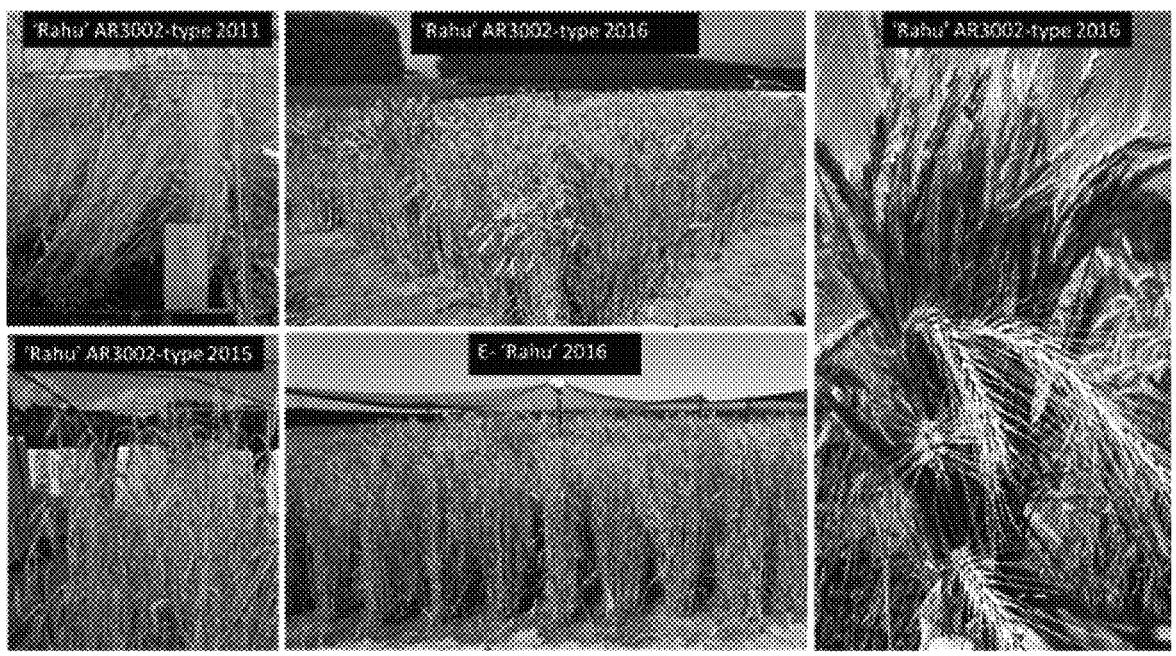
FIG. 2. Symbiotic associations of *S. cereale* and *Epichloë* endophytes showing substantially normal phenotypes.

A summary of successful inoculations marked with "Yes" is included in Table 4 for those endophyte strains where at least some of the inoculated plants were of substantially normal phenotype and were able to progress through a normal life cycle (FIG. 2). Seeds were collected from the plants as indicated in Table 4.

TABLE 4

Strains inoculated into and infecting *S. cereale* and examples of seed production in *S. cereale*.

| Endophyte | Inoculation of Secale attempted | Infected plants of Secale obtained | Infected plants of Secale produced seed | Seed of Secale was infected with endophyte | Seed was infected with viable endophyte |
| --- | --- | --- | --- | --- | --- |
| AR3002 | Yes | Yes | Yes | Yes | Yes |
| AR3005 | Yes | Yes | Yes | Yes | Yes |

TABLE 4-continued

Strains inoculated into and infecting *S. cereale* and examples of seed production in *S. cereale*.

| Endophyte | Inoculation of Secale attempted | Infected plants of Secale obtained | Infected plants of Secale produced seed | Seed of Secale was infected with endophyte | Seed was infected with viable endophyte |
| --- | --- | --- | --- | --- | --- |
| AR3007 | Yes | Yes | Yes | Yes | Yes |
| AR3042 | Yes | Yes | Yes | Yes | Yes |

Example 6

Alkaloid Production in Endophyte Infected Natural Host Plants

A range of host plants were examined for the presence of loline alkaloids, peramine, ergot alkaloids, and indole diterpenes by minor modifications of established methods (Kennedy and Bush, 1983; Yates et al., 1989: Rasmussen et al., 2012). The results are in Table 5 for selected endophytes of this study with those endophyte alkaloids detected named under the alkaloid class. These results show that a number of isolated strains of *Epichloë* endophytes as described herein, and particularly those that are AR3002 type as defined by the SSR data presented elsewhere herein, when in planta, may confer upon the symbiotic combination a capacity to produce measurable amounts of chanoclavine, paspaline, terpendole E or a combination thereof.

TABLE 5

Detection of endophyte alkaloids for endophyte-infected parent *Elymus* plants.

| Endophyte Strain | Host plant species | Indole Diterpenes | Ergot Alkaloids | Lolines[1] | Peramine |
|---|---|---|---|---|---|
| AR3002 | *Elymus dahuricus* | Paspaline, Terpendole E | Chanoclavine | | |
| AR3005 | *Elymus* sp. | Paspaline, Terpendole E | Chanoclavine | | |
| AR3007 | *Elymus dahuricus* | Paspaline, Terpendole E | Chanoclavine | | |
| AR3042 | *Elymus dahuricus* | Paspaline, Terpendole E | Chanoclavine | | |
| AR3046 | *Elymus mutabilis* | | Chanoclavine | NFL | Peramine |
| AR3050 | *Elymus mutabilis* | | Chanoclavine | NFL | Peramine |
| AR3049 | *Elymus mutabilis* | | Chanoclavine | NFL | Peramine |
| AR3078 | *Elymus nevskii* | | Chanoclavine | NFL | Peramine |
| AR3073 | *Elymus caninus* | | Chanoclavine | NFL | Peramine |
| AR3064 | *Elymus mutabilis* | | Chanoclavine | NFL | Peramine |
| AR3067 | *Elymus uralensis* | | Chanoclavine | NFL | Peramine |
| AR3074 | *Elymus caninus* | | Chanoclavine | NFL | Peramine |
| AR3076 | *Elymus mutabilis* var. *oschensis* | | Chanoclavine | NFL | Peramine |
| AR3039 | *Elymus caninus* | | Chanoclavine | | Peramine |

Footnote:
[1]NFL = N-formylloline.

Example 7

Source and Geographic Origin of Selected Endophytes from *Elymus* Spp.

Table 6 shows the source accession number from which the isolated strains of *Epichloë* endophyte as described herein were obtained, the species of the natural host plant accession, and the regional source of the accession.

TABLE 6

Strains of isolated endophytes by AR code number, original putative host species, regional source, and source accession number.

| Endophyte | *Elymus* Host | Region | Source accession |
|---|---|---|---|
| AR3002 | *E. dahuricus* | CHINA | BZ2155 |
| AR3005 | *E.* spp. | CHINA | BZ2159 |
| AR3007 | *E. dahuricus* | CHINA | BZ2162 |
| AR3042 | *E. dahuricus* | CHINA | BZ2162 |

Example 8

Alkaloid Production in *Secale cereale* Plants

Seedlings of *S. cereale* cultivar Rahu were inoculated with AR3002, AR3005, AR3007, and AR3042, allowed to mature and seed containing a combination of all endophytes was collected. After seed increase, sufficient seed was available to plant a replicate trial at Lincoln, Canterbury, New Zealand. The trial was designed to allow assessment of *S. cereale* (cultivar Rahu) infected with a range of the isolated strains of *Epichloë* endophyte as described herein under a range of common management practices. Samples were taken at various stages for silage or grain, and were analysed for alkaloid content by minor modifications of established methods (Kennedy and Bush, 1983; Yates et al., 1989: Rasmussen et al., 2012) (as described in Table 7).

TABLE 7

Alkaloid analysis observations of *S. cereale* plants (average of 4 plots, SEM provided in brackets) infected with AR3002 type endophytes. AR3002 bulk and AR3002 elite refer to *S. cereale* plant samples analysed in this table that contain a combination of AR3002, AR3005, AR3007, and AR3042 endophytes. The terms "elite" and "bulk" refer to two different successive generations of *S. cereale* plants selected for improved endophyte transmission and phenotype. Results for chanoclavine are presented as µg/g, while paspaline and terpendole E are presented as peak area normalised for sample weight.
Table 7.

| Harvest | AR3002 rye line | Plant Part | Paspaline (rel. peak area) | Terpendole E (rel. peak area) | Chanoclavine (µg/g) |
|---|---|---|---|---|---|
| Early Green Chop Silage | AR3002 (elite) | Tiller | 1.74 (0.15) | 84.9 (13.0) | 0.18 (0.004) |
| | AR3002 (bulk) | Tiller | 1.58 (0.21) | 101.6 (9.4) | 0.15 (0.03) |
| | AR3002 (elite) | Tiller | 2.48 (0.22) | 88.9 (18.4) | 0.22 (0.08) |

TABLE 7-continued

Alkaloid analysis observations of *S. cereale* plants (average of 4 plots, SEM provided in brackets) infected with AR3002 type endophytes. AR3002 bulk and AR3002 elite refer to *S. cereale* plant samples analysed in this table that contain a combination of AR3002, AR3005, AR3007, and AR3042 endophytes. The terms "elite" and "bulk" refer to two different successive generations of *S. cereale* plants selected for improved endophyte transmission and phenotype. Results for chanoclavine are presented as µg/g, while paspaline and terpendole E are presented as peak area normalised for sample weight.
Table 7.

| Harvest | AR3002 rye line | Plant Part | Paspaline (rel. peak area) | Terpendole E (rel. peak area) | Chanoclavine (µg/g) |
|---|---|---|---|---|---|
| | AR3002 (bulk) | Tiller | 2.18 (0.16) | 94.6 (2.1) | 0.18 (0.02) |
| Mid-Spring Green | AR3002 (elite) | Tiller | 0.82 (0.09) | 20.9 (3.1) | 0.12 (0.02) |
| Chop Silage | AR3002 (bulk) | Tiller | 0.78 (0.17) | 27.3 (5.3) | 0.11 (0.02) |
| | AR3002 (elite) | Tiller | 1.19 (0.18) | 10.9 (1.5) | 0.07 (0.02) |
| | AR3002 (bulk) | Tiller | 2.75 (0.87) | 31.5 (1.9) | 0.14 (0.01) |
| Whole Cereal Silage | AR3002 (elite) | Tiller | 0.461 (0.022) | 35.7 (4.6) | 0.028 (0.002) |
| | AR3002 (bulk) | Tiller | 0.404 (0.025) | 34.7 (1.4) | 0.025 (0.003) |
| Grain Harvest | AR3002 (elite) | Seed | 1.24 (0.10) | 10.6 (1.3) | 0.07 (0.01) |
| | AR3002 (elite) | Stalk | 2.09 (0.20) | 63.0 (4.6) | 0.12 (0.02) |
| | AR3002 (bulk) | Seed | 3.91 (1.47) | 33.8 (5.5) | 0.11 (0.03) |
| | AR3002 (bulk) | Stalk | 1.42 (0.35) | 55.7 (6.5) | 0.13 (0.02) |

Example 9

*Secale cereale*/AR3002/Endophyte Combinations Having Bioactivity Against Cereal Pests Methods:

The ability of the *Epichloë* endophyte AR3002 to confer at least some level of pest resistance to a host plant was tested by challenging *S. cereale* cultivar Rahu and *S. cereale* cultivar Amilo infected with AR3002 with Argentine stem weevil (ASW) (*Listronotus bonariensis*) and with natural infestations of two fly species: *Cerodontha australis* (wheat sheath leaf miner) and *Mayetiola destructor* (Hessian fly). Infected plants were tested in pot experiments as shown in FIG. 1.

Two experiments were carried out using ASW and either AR3002 infected Rahu or Amilo.

In the first experiment, treatments were: Rahu without endophyte (Nil); Rahu infected with strain AR3002 and Rahu infected with a loline-producing endophyte. This loline producing endophyte is used in this comparative example to demonstrate the effects of alkaloids produced in plant/endophyte symbioses that are known to deter insect herbivory (i.e. loline). Rahu plants infected with AR3002 (15 replicates), Nil (15 replicates) and the loline producing endophyte (13 replicates) were arranged in pots (12 cm diameter) in a randomised block design on the floor of a screenhouse. Six field collected adult ASW were placed on each plant. The entire trial was covered with fine nylon material to contain the ASW.

After two weeks, the cover was removed and the number of adult feeding scars on 10 tillers on each plant, and the number of eggs on each plant, were counted. Plants were then left uncovered for 18 days after which all tillers were removed from each plant by cutting below the base of the aerial portion of the plant. For each plant the number of live and dead tillers were counted to determine the live:dead tiller ratio. Then, 20 tillers in the same live:dead tiller ratio were examined by dissection for larval damage. ASW larval damage was scored as follows: minor where there was external feeding only, moderate where the larva had penetrated and partially mined the tiller, and severe where the tiller was extensively mined or had a hole bored through the meristem.

In the second experiment, treatments were: Amilo without endophyte (Nil); Amilo infected with strain AR3002; and Rahu without endophyte (Nil). Rahu Nil was included as a comparison with the previous experiment. The experiment was set up in the same way as the Rahu experiment using the same number of replicates and pot arrangement with one difference—ASW adults were caged onto each pot using fine nylon net. All measurements were the same as in the Rahu experiment except that adult feeding and oviposition were assessed after 3 weeks on 6 tillers/plant and larval damage after a further 4 weeks.

In both experiments, natural fly infestations were recorded when larvae, pupae or symptoms of presence (frass) were found in the 20 tillers examined from each plant. In the Rahu experiment, all fly larvae found were *Cerodontha australis* whereas in the Amilo experiment both *C. australis* and *M. destructor* were found.

Statistical Analysis:

For Argentine stem weevil, adult feeding and the number of eggs per plant, and the total percentage of tillers damaged by larvae and the percentage that had moderate or severe damage were analysed by ANOVA. As there were significant differences in the number of live tillers/plant, the number of adult feeding scars/plant calculated from the assessment of tillers was analysed using the total number of tillers/plant as a covariate. The number of fly-infested tillers were also analysed by ANOVA. For the Amilo trial, the data on the larvae of the two fly species were combined as data were too sparse to be analysed separately and were log transformed before analysis by ANOVA. A binomial analysis on whether flies were present or not was also carried out due to a high proportion of some plants infected with endophytes having no flies present.

Results:

In the experiment with Rahu, there were significantly fewer Argentine stem weevil adult feeding scars on plants infected with the loline producing endophyte than on uninfected plants (Nil) and AR3002 (P=0.016) (Table 8). There was no significant difference between treatments in the number of eggs/plant P>0.05). Both total larval feeding damage and the moderate and severe feeding damage was significantly reduced (P=0.014 & P=0.004 respectively) in AR3002 and the loline producing endophyte infected plants as compared with uninfected plants (Nil) (FIGS. 1A & B).

In the cultivar Amilo, adult feeding was significantly less on plants infected with AR3002 than on uninfected Amilo (Nil) and Rahu (Nil) (P=0.016) (Table 8). The number of eggs per plant did not differ between treatments. The percentage of tillers with any level of Argentine stem weevil damage was significantly less on plants infected with AR3002 as compared to uninfected Rahu (Nil) and uninfected Amilo (Nil) (FIG. 1B). Taking only those tillers that were moderately and severely damaged, AR3002-infected plants had a lower percentage of damaged tillers than the two Nil treatments (P=0.012 and P=0.002 respectively).

considerably from plants infected with endophyte, regardless of strain. The relatively low percentage of Rahu Nil infested with flies in the Amilo trial probably reflects the age of the plants and the probability that they had been infested earlier in the season. Of the 56 fly larvae and pupae found in the Amilo trial, 31 were identified as *C. australis* and 25 as *M. destructor* based on morphology. One specimen of each species was confirmed by genotyping. Neither of the two species were found infesting plants infected with AR3002, whereas the mean number/plant on Amilo Nil was 3.19 for *C. australis* and 3.12 for *M. destructor*. We can conclude from this that AR3002 provides resistance to both fly species.

Example 10

*Secale cereale*/AR3002/Endophyte Combinations Having Bioactivity Against *Thrips*

Methods:

The ability of the *Epichloë* endophyte AR3002 to confer at least some level of pest resistance to a host plant was tested by challenging *S. cereale* cultivar Rahu infected with AR3002 with natural infestations of *thrips* (*Frankliniella* sp., order Thysanoptera).

One experiment was carried out using *thrips* and AR3002-infected rye.

Treatments were: rye without endophyte (Nil); 2 lines of rye infected with AR3002 (elite and bulk); and rye infected with strain a loline-producing endophyte. The loline producing endophyte is used in this comparative example to

TABLE 8

Number of adult Argentine stem weevil (ASW) feeding scars (FS) and number of eggs laid, and the number of stem boring flies and percentage of plants infested with flies in *S. cereale* cultivar Rahu and cultivar Amilo.

|  | No. ASW FS/Plant | No. ASW Eggs/Plant | No. Flies/plant | Log No. Flies/plant | % Plants with flies present |
|---|---|---|---|---|---|
| Rahu Trial |  |  |  |  |  |
| AR3002 | 11.2 | 2.3 | 0.2 |  | 7.1 |
| Loline producing endophyte | 1.0 | 0.9 | 0.3 |  | 16.7 |
| Nil | 16.3 | 2.8 | 11.7 |  | 92.9 |
| SED | 3.16 | 1.00 | 2.33 |  | 8.94 |
| P | <0.001 | 0.170 | <0.001 |  | <0.001 |
| Amilo Trial |  |  |  |  |  |
| Amilo AR3002 | 35.1 | 3.1 | 0 | 0 | 0 |
| Amilo Nil | 81.3 | 5.0 | 6.3 | 0.65 | 82.6 |
| Rahu Nil | 64.4 | 4.2 | 1.3 | 0.19 | 32.6 |
| SED | 13.12 | 2.43 | 1.78 | 0.115 | 0.02 |
| P | 0.016 | 0.884 | 0.004 | <0.001 | <0.001 |

The wheat sheath leaf miner (*C. australis*) was the only fly species present in the Rahu trial whereas Hessian flies (*M. destructor*) were also present in the Amilo trial. The data for the two species of flies in the Amilo trial were combined to give a total number of larvae and pupae.

The number of flies/plant was calculated from the number in the tillers examined per plant, and was found to be significantly lower in all endophyte-infected plants as compared to uninfected (Nil) plants.

The number of flies did not differ significantly between AR3002 infected plants and plants infected with the loline producing endophyte in Rahu (Table 8). The percentage of Nil plants with flies present was very high and differed demonstrate the effects of alkaloids produced in plant/endophyte symbioses that are known to deter insect herbivory (i.e. lolines). Rye plants for each treatment were arranged three to a pot (10 cm diameter) with six replicate pots per treatment arranged in a randomised block design within a controlled growth chamber (22-24° C., 60-70% relative humidity).

After six weeks, four leaves from each plant (a total of 12 leaves per pot from three plants) were removed from separate tillers by cutting them at the ligule using a scalpel blade. These leaves were attached to blank A4 sheets of paper using small amounts polypropylene-based, pressure-sensitive tape (Sellotape) at each end of the leaf. The number of *thrips* were then counted on the top side of each leaf with the aid of a dissecting microscope and forceps. The area of each leaf was then calculated (approximately) from measurements of the length and maximum width of each leaf using a ruler. The density of *thrips* per $cm^2$ of leaf tissue was then calculated. A separate set of four tillers per plant (12 per pot) were then assessed for endophyte presence using a standard tissue-print immunoblot technique.

Statistical Analysis:

The *thrips* data was analysed by ANOVA followed by Fisher's protected least significant difference (LSD) test to determine significant (P<0.05) differences between treatment means.

Results:

There were significantly fewer *thrips* on plants infected with AR3002 (elite and bulk) than on uninfected plants (Nil) and those infected with the loline producing endophyte (P<0.001) (Table 9). We can conclude from this that AR3002 provides resistance to *Frankliniella* species.

TABLE 9

Mean number of thrips observed on *S. cereale* cultivar Rahu (means in a column followed by the same letter are not significantly different at P ≤ 0.05 according to Fisher's protected LSD test).

| | Mean number of thrips per $cm^2$ leaf tissue | Grouping |
|---|---|---|
| Uninfected (Nil) | 0.55 | A |
| Loline producing endophyte | 0.45 | A |
| AR3002 (elite) | 0.22 | B |
| AR3002 (bulk) | 0.13 | B |
| P-value | <0.001 | |

Example 11

Disease Resistance in *Secale cereale*/Endophyte Combinations

A field trial was undertaken at the AgResearch Lincoln Research Farm, New Zealand, using a total of seven lines of forage rye *Secale cereale* cultivar "Rahu" which included two lines of AR3002 (elite and bulk), along with a three nil endophyte (endophyte-free) lines (Table 10). The trial was sown on 13 May 2016 in plots (8 m×1.35 m) with 15 cm row spacings. The soil type was a Templeton silt loam.

No slug/snail bait, fungicides or insecticides were applied to the trial. The trial received best-practice applications of fertiliser, herbicides and plant growth regulators. The trial area was irrigated regularly to avoid moisture stress and was covered with bird netting on 8 November.

Statistical analysis was completed with GenStat® (version 18, VSN International Ltd, UK) using a one-way ANOVA model. Significant differences were separated using least significant difference (LSD) tests (P=0.05).

TABLE 10

Rahu treatment names, germination tests, viable endophyte of seed lines pre-season and endophyte-infected tiller tests (immuno-blot) of plots in early October 2016.

| Treatment Name | Rahu Treatment | Accession Number | Germination (%)$^a$ | Thousand Seed Weight (g)$^b$ | Viable Endophyte (%) | Endophyte-infected tillers (%) early October 2016 |
|---|---|---|---|---|---|---|
| AR3002 (elite) | Elite AR3002 type (AR3002, AR3005, AR3007, AR3042) | BZ14877 | 87 | 24.43 | 100$^c$ | 98 |
| AR3002 (bulk) | Bulk AR3002 type (AR3002, AR3005, AR3007, AR3042) | BZ14789 | 81 | 21.20 | 100$^d$ | 100 |
| Nil - line 1 | Bulk Nil | BZ14792 | 90 | 32.20 | 0$^d$ | 0 |
| Nil - line 2 | Commercial seed - 1 (Nil) | BZ15483 | 91 | 27.84 | Not tested | 0 |
| Nil - line 3 | Commercial seed - 2 (Nil) | BZ15484 | 88 | 19.96 | Not tested | 0 |

$^a$Germination test (100 grain per line left for 7 days germ)
$^b$Count of 500 seeds per treatment
$^c$By seed squash along with some isolation tests
$^d$ By tiller blot of seedlings in glasshouse grow out test Disease Incidence:

Disease incidence was assessed on two separate occasions in spring 2016. In total this experiment was comprised of 7 lines (treatments), which included two lines of AR3002 (elite and bulk) along with three nil endophyte (endophyte-free) lines.

Visual disease assessments, based on the percentage of leaf area affected on leaves on the main stem, showed infection by leaf streak *Cercosporidium graminis* and leaf rust *Puccinia recondita* (James, 1971). Diagnosis was confirmed by Mark Braithwaite of Plant Diagnostics Limited. Leaf streak has been found in rye (Braithwaite et al. 1998).

At each assessment, 10 main stems (tillers) were randomly selected per plot and the % disease infection was recorded on the top three leaves that were showing signs of infection.

Assessment 1 at Grow Stage 45-55, 17 Oct. 2016.

At this assessment, both leaf streak and leaf rust diseases were identified on leaves 3, 4 and (Tables 11a and b).

The lines infected with AR3002 on average had significantly less leaf streak disease than the nil lines for all three leaves (Table 11a) (P<0.05). The same was the case for leaf rust (Table 11b) (P<0.05).

TABLE 11a

Effect of endophyte on severity (% leaf area affected) by leaf streak (*Cercosporidium graminis*) on rye cultivar Rahu, assessed 17 Oct. 2016. AR3002 is the mean of two lines and Nil is the mean of 3 lines.

| Treatment | Leaf 3 †‡ | Leaf 4 †‡ | Leaf 5 †‡ |
|---|---|---|---|
| AR3002 | 0.007 b | 0.028 b | 0.052 b |
| Nil | 0.345 a | 0.585 a | 1.308 a |
| P-value | <0.001 | <0.001 | 0.001 |

† back-transformed means after log transformation (a constant value of 0.5 was added to all values to allow the log transformation of zero values).
‡ Means within a column that do not share a letter are significantly different at 5% probability.

TABLE 11b

Effect of endophyte on severity (% leaf area affected) by leaf rust (*Puccinia recondita*) on rye cultivar Rahu, assessed 17 Oct. 2016. AR3002 is the mean of two lines and Nil is the mean of three lines.

| Treatment | Leaf 3 ‡ | Leaf 4 †‡ | Leaf 5 †‡ |
|---|---|---|---|
| AR3002 | 0.151 b | 0.280 b | 0.331 b |
| Nil | 0.692 a | 0.836 a | 0.916 a |
| P-value | 0.022 | 0.009 | 0.007 |

† back-transformed means after log transformation (a constant value of 0.5 was added to all values to allow the log transformation of zero values).
‡ Means within a column that do not share a letter are significantly different at 5% probability.

Assessment 2 at Grow Stage 65 (Anthesis), 7 Nov. 2016.

At this assessment, leaf streak and leaf rust were observed on leaves 1, 2 and 3. As with assessment 1, significantly less disease was observed in rye lines containing AR3002 endophyte compared with nil lines in all cases except leaf 1 for leaf streak (Tables 12a and b) (P<0.05).

TABLE 12a

The effect of endophyte on severity (% leaf area affected) by leaf streak (*Cercosporidium graminis*) on rye cultivar Rahu, assessed 7 Nov. 2016. AR3002 is the mean of two lines and Nil is the mean of three lines.

| Treatment | Leaf 14 ‡ | Leaf 2 †‡ | Leaf 3 †‡ |
|---|---|---|---|
| AR3002 | 0.000 b | 0.043 b | 0.355 b |
| Nil | 0.033 b | 0.618 a | 2.571 a |
| P-value | 0.027 | 0.007 | 0.002 |

† back-transformed means after log transformation (a constant value of 0.5 was added to all values to allow the log transformation of zero values).
‡ Means within a column that do not share a letter are significantly different at 5% probability.

TABLE 12b

Effect of endophyte on severity (% leaf area affected) by leaf rust (*Puccinia recondita*) on rye cultivar Rahu, assessed 7 Nov. 2016. AR3002 is the mean of two lines and Nil is the mean of three lines.

| Treatment | Leaf 1 †‡ | Leaf 2 †‡ | Leaf 3 †‡ |
|---|---|---|---|
| AR3002 | 0.430 b | 1.328 b | 2.646 b |
| Nil | 1.040 a | 4.589 a | 13.471 a |
| P-value | 0.009 | <0.001 | <0.001 |

† back-transformed means after log transformation (a constant value of 0.5 was added to all values to allow the log transformation of zero values).
‡ Means within a column that do not share a letter are significantly different at 5% probability.

Example 12

Yield in *Secale cereale*/Endophyte Combinations

In the same experiment detailed in Example 11, above, agronomic traits were also assessed. In total this experiment was comprised of 7 lines (treatments), which included two lines of AR3002 (elite and bulk) along with three nil endophyte (endophyte-free) lines.

Half the length (4 m) of each plot was used to assess forage yields (with some grain production) and the remaining half (4 m) was used solely for assessing grain production. The sequence of forage cuts and grain harvesting managements are outlined in table 13. Quadrat cuts were used to subsample and assess the plots.

TABLE 13

Diagrammatic representation of forage and grain production treatments in the 2016-17 season in the field at AgResearch Lincoln.

| Management | 13 May | 5 Sept | 3 Oct | 30 Dec. 2016/17 Jan. 2017 | 20 Feb |
|---|---|---|---|---|---|
| 1A Forage | Sown | → Early green chop silage | → | Whole crop cereal silage | |
| 1B Forage + Grain | Sown | → Early green chop silage | → | | Grain |
| 2 Grain-only | Sown | → | | | Grain |

Yields of Early Spring Green Chop Silage Followed by Whole Crop Cereal Silage (Management '1A Forage')

Forage yields were statistically similar at the first harvest in early spring for AR3002 and Nil (Table 14). However, when the regrowth was harvested in early summer as whole crop cereal silage, AR3002 was statistically higher yielding than Nil, and this was also reflected in the overall total yields for this forage management treatment for the 2016-17 year (Table 14).

TABLE 14

Forage yield for management treatment '1A Forage' harvested as green chop silage in early spring followed by whole crop cereal silage in early summer, and overall total yield, at Lincoln. AR3002 is the mean of two lines and Nil is the mean of three lines.

| Endophyte treatment | Yield at early spring green chop silage (t/ha) ‡ | Yield at whole crop cereal silage (t/ha) ‡ | Total yield (t/ha) †‡ |
|---|---|---|---|
| AR3002 | 2.914 a | 9.303 a | 12.158 a |
| Nil | 3.451 a | 2.756 b | 6.184 b |
| P-value | 0.167 | <0.001 | <0.001 |

‡ Means within a column that do not share a letter are significantly different at 5% probability,
† back-transformed means after square root transformation.

Yields of Early Spring Green Chop Silage (Management '1B Forage')

AR3002 and Nil plots yielded statistically similar amounts when harvested in early spring as green chop silage (Table 15).

TABLE 15

Forage yield for management treatment '1B Forage' as harvested as green chop silage in early spring at Lincoln, 5 Sep. 2016. AR3002 is the mean of two lines and Nil is the mean of three lines.

| Endophyte treatment | Yield at early green chop silage (t/ha) †‡ |
|---|---|
| AR3002 | 2.992 a |
| Nil | 4.173 a |
| P-value | 0.070 |

‡ Means within a column that do not share a letter are significantly different at 5% probability,
† back-transformed means after square root transformation.

Grain and Straw Yields (Managements 1B Forage and 2 Grain-Only)

Table 18 presents the grain and straw yield results for the two grain management treatments:

1B (Forage+Grain): a forage harvest in early spring followed by grain harvest in late summer; and 2 (Grain-only): a grain harvest in late summer (i.e. no harvest for forage).

AR3002 plots yielded significantly more grain and straw than endophyte-free (Nil) under both management regimes (Table 18) (P<0.05).

TABLE 18

Grain and straw yields for management treatments 1B and 2 as harvested at Lincoln, 20 Feb. 2017. AR3002 is the mean of two lines and Nil is the mean of three lines.

| | Management treatment | | | |
|---|---|---|---|---|
| | 1B Forage + Grain | | 2 Grain-only production | |
| Endophyte treatment | Grain yield (t/ha) ‡ | Straw yield (t/ha) ‡ | Grain yield (t/ha) ‡ | Straw yield (t/ha) ‡ |
| AR3002 | 1.774 a | 6.360 a | 5.475 a | 14.064 a |
| Nil | 0.958 b | 2.897 b | 4.222 b | 6.547 b |
| P-value | 0.008 | <0.001 | <0.001 | <0.001 |

‡ Means within a column that do not share a letter are significantly different at 5% probability.

The results of the experiments detailed above show, quite unexpectedly, that certain *Epichloë* endophytes have the ability to confer onto a host plant, at least some level of pest and disease protection and/or resistance. Moreover, quite surprisingly, the inventors have found that certain *Epichloë* endophytes also have the ability to improve the agronomic traits of a host plant, particularly a cereal plant, and most particularly *Secale*.

Example 13

Effects of "Rahu" *Secale* Infected with Endophyte AR3002 on Saw-Toothed Grain Beetle This study assessed the ability of endophyte-infected 'Rahu' rye to act as a feeding deterrent of saw toothed grain beetles relative to endophyte-free 'Rahu' rye.

Background:

Saw toothed grain beetles *Oryzaephilus surinamensis* (Linnaeus) are a commonly encountered secondary pest of stored grain in New Zealand. Current insect control strategies are heavily based on the organophosphate pirimiphos-methyl. With long term use of organophosphates under review internationally and in New Zealand and anecdotal reports of resistance to pirimiphos-methyl, the development of alternative control strategies is important for continued successful grain storage.

300 g of grain was lightly ground before 40 live, mixed sex adult saw toothed grain beetles were added to each pot. Pots were kept at 23° C. at 65% relative humidity for the duration of the trial. Insects were counted by sieving through a nest of sieves to separate insects from grain. Insects were counted 2 months after filling. This experiment was a randomised complete block with 5 replicates and 4 treatments. Results are shown in table 19.

TABLE 19

Saw toothed grain beetles alive after 2 months of grain storage

| Trt Name | Alive | Total |
|---|---|---|
| AR3002 (15/16) | 164 ab | 191 ab |
| AR3002 (16/17) | 121 a | 146 a |
| Loline producing endophyte | 264 c | 341 c |
| Nil | 230 be | 248 b |
| Mean | 195 | 232 |
| SD | 64.3 | 84.1 |
| Fpr | 0.037 | 0.003 |
| LSD | 99.8 | 85.6 |
| CV % | 36.9 | 26.2 |

After two months, the beetle population increased from 40 live insects to 121-264 live insects in the loline producing endophyte pots. There were fewer live (P=0.037) and total (P=0.003) insects in the AR3002 lines relative to the loline producing endophyte and nil endophyte Rahu lines.

CONCLUSIONS

There were fewer live and total insects at two months after filling in AR3002 infected lines, which was significantly different, compared to the nil endophyte lines.

Although the invention has been described by way of example and with reference to particular embodiments, it is to be understood that modifications and/or improvements may be made without departing from the scope of the invention.

In addition, where features or aspects of the invention are described in terms of Markush groups, those skilled in the art will recognise that the invention is also thereby described in terms of any individual member or subgroup of members of the Markush group.

INDUSTRIAL APPLICATION

The isolated *Epichloë* endophyte strains, plant/*Epichloë* endophyte combinations, seeds infected with *Epichloë* endophytes, and methods of making and using such combinations according to the invention as disclosed herein all have industrial application for the production of plants that are used for human or animal consumption.

REFERENCES

Bacetty A A, Snook M E, Glenn A E, Noe J P, Hill N, Culbreath A, Timper P, Bacon C W (2009a) Toxicity of endophyte-infected tall fescue alkaloids and grass metabolites on *Pratylenchus scribneri*. Phytopathology 99: 1336-1345

Bacetty A A, Snook M E, Glenn A E, Noe J P, Nagabhyru P, Bacon C W (2009b) Chemotaxis disruption in *Pratylenchus scribneri* by tall fescue root extracts and alkaloids. Journal of Chemical Ecology 35: 844-850

Blankenship J D, Spiering M J, Wilkinson H H, Fannin F F, Bush L P, Schardl C L (2001). Production of loline alkaloids by the grass endophyte, *Neotyphodium uncinatum*, in defined media. Phytochemistry 58: 395-401

Brownstein M J, Carpten J D, Smith J R (1996) Modulation of non-templated nucleotide addition by Taq DNA polymerase: Primer modifications that facilitate genotyping. BioTechniques 20: 1004-1010

Bush L P, Wilkinson H H, Schardl C L (1997) Bioprotective Alkaloids of Grass-Fungal Endophyte Symbioses. Plant Physiology 114: 1-7

Card S D, Faville M J, Simpson W R, Johnson R D, Voisey C R, De Bonth A C M and D E Hume. (2014) Mutualistic fungal endophytes in the Triticeae—survey and description. FEMS Microbiology Ecology 88: 94-106

Casida J E, Quistad G B (1998) Golden Age of Insecticide Research: Past, Present, or Future? Annual Review of Entomology 43: 1-16.

Christensen M J (1995) Variation in the ability of *Acremonium* endophytes of *Lolium perenne, Festuca arundinacea* and *F. pratensis* to form compatible associations in the 3 grasses. Mycological Research 99: 466-470

Christensen M J, Bennett R J, Schmid J (2002) Growth of *Epichloë/Neotyphodium* and p-endophytes in leaves of *Lolium* and *Festuca* grasses. Mycological Research 106: 93-106

Christensen M J, Bennett R J, Schmid J (2001) Vascular bundle colonisation by *Neotyphodium* endophytes in natural and novel associations with grasses. Mycological Research 105: 1239-1245

Christensen M J, Leuchtmann A, Rowan D D, Tapper B A (1993) Taxonomy of *Acremonium* Endophytes of Tall Fescue (*Festuca-Arundinacea*), Meadow Fescue (*F-Pratensis*) and Perennial Rye-Grass (*Lolium-Perenne*). Mycological Research 97: 1083-1092

Christensen M J, Simpson W R, Al Samarrai T (2000) Infection of tall fescue and perennial ryegrass plants by combinations of different *Neotyphodium* endophytes. Mycological Research 104: 974-978

Christensen M J, Saulsbury K, Simpson W R (2012) Conspicuous epiphytic growth of an interspecific hybrid *Neotyphodium* sp. endophyte on distorted host inflorescences. Fungal Biology 116: 42-48

Felsenstein, J. (2005) PHYLIP (Phylogeny Inference Package) version 3.6. Distributed by the author. Department of Genome Sciences, University of Washington, Seattle Glenn A E, Bacon C W, Price R, Hanlin R T (1996) Molecular phylogeny of *Acremonium* and its taxonomic implications. Mycologia 88: 369-383

Huson D, Richter D, Rausch C, Dezulian T, Franz M, Rupp R (2007) Dendroscope: An interactive viewer for large phylogenetic trees. BMC bioinformatics 8: 460

Kennedy C W, Bush L P (1983) Effect of environment and management factors on the accumulation of N-acetyl and N-formyl loline alkaloids in tall fescue. Crop Science 23: 547-552

Kirkby K A, Pratley J E, Hume D E, Faville M J, An M and H. Wu. (2011) Incidence of endophyte *Neotyphodium occultans* in *Lolium rigidum* from Australia. Weed Research 51: 261-272

Koulman A, Lane G A, Christensen M J, Fraser K, Tapper B A (2007) Peramine and other fungal alkaloids are exuded in the guttation fluid of endophyte-infected grasses. Phytochemistry 68: 355-360

Latch G C M, Christensen M J (1985) Artificial Infection of Grasses with Endophytes. Annals of Applied Biology 107: 17-24

Leuchtmann A, C W Bacon, C L Schardl, J F White and M Tadych. 2014. Nomenclatural realignment of *Neotyphodium* species with genus Epichloe. Mycologia 106: 202-215.

Malinowski D P, Belesky D P (2000) Adaptations of endophyte-infected cool-season grasses to environmental stresses: Mechanisms of drought and mineral stress tolerance. Crop Science: 40: 923-940 Marshall D, Tunali B, Nelson L R (1999) Occurrence of fungal endophytes in species of wild *triticum*. Crop Science 39: 1507-1512

Miller J S, Funk V A, Wagner W L, Barrie F, Hoch P C, Herendeen P (2011) Outcomes of the 2011 botanical nomenclature section at the XVIII International Botanical Congress. PhytoKeys 5: 1-3

Moon C D, Tapper B A, Scott B (1999) Identification of *Epichloë* endophytes in planta by a microsatellite-based PCR fingerprinting assay with automated analysis. Applied and Environmental Microbiology 65: 1268-1279

Moon C D, Craven K D, Leuchtmann A, Clements S L, Schardl C L (2004). Prevalence of interspecific hybrids amongst asexual fungal endophytes of grasses. Molecular Ecology 13 (6): 1455-1467

Porter J K (1994). Chemical constituents of grass endophytes. In: Bacon, C. W., White Jr., J. F (Eds), Biotechnology of Endophytic Fungi of Grasses. CRC, Boca Raton, F L, pp. 103-123

Rasmussen S, Lane G A, Mace W, Parsons A J, Fraser K, Xue H. (2012) The use of genomics and metabolomics methods to quantify fungal endosymbionts and alkaloids in grasses. Methods in Molecular Biology 860: 213-226

Rowan D D (1993) Lolitrems, peramine and paxilline: mycotoxins of the ryegrass/endophyte interaction. Agriculture, Ecosystems and Environment 44: 103-122

Rowan D D, Latch G C M (1994) Utilization of endophyte-infected perennial ryegrasses for increased insect resistance. In: Bacon C W, White Jr. J F (eds), Biotechnology of Endophyte Fungi of Grasses. CRC Press, Boca Raton, Fonda, pp. 169-183

Sanger F, Nicklen S, Coulson A R (1977), DNA sequencing with chain-terminating inhibitors, Proceedings of the National Academy of Sciences USA 74 (12): 5463-5467

Schardl C L, Craven K D, Speakman S, Stromberg A, Lindstrom A, Yoshida R (2008). A novel test for host-symbiont codivergence indicates ancient origin of fungal endophytes in grasses. Syst Biol. 57: 483-498

Schardl C L, Grossman R B, Nagabhyru P, Faulkner J R, Mallik U P (2007) Loline alkaloids: Currencies of mutualism. Phytochemistry 68: 980-996

Schardl C L, Young C A, Faulkner J R, Florea S, Pan J (2012) Chemotypic diversity of *Epichloë* fungal symbionts of grasses. Fungal Ecology 5: 331-344

Schuelke M (2000) An economic method for the fluorescent labelling of PCR fragments. Nature Biotechnology 18: 233-234

Simpson W R, Mace W J (2012) Novel associations between *Epichloë* endophytes and grasses: Possibilities and outcomes. In '*Epichloë*, endophytes of cool season grasses: Implications, utilization and biology.' (Eds C A Young, G E Aiken, R L McCulley, J R Strickland, C L Schardl.) pp. 35-39. (The Samuel Roberts Noble Foundation: Ardmore, Oklahoma)

Simpson W R, Schmid J, Singh J, Faville M J, Johnson R D (2012) A morphological change in the fungal symbiont *Neotyphodium lolli* induces dwarfing in its host plant *Lolium perenne*. Fungal Biology 116: 234-240

Subramanian A R, Kaufmann M, Morgenstern B (2008) DIALIGN-TX: greedy and progressive approaches for segment-based multiple sequence alignment. Algorithms for Molecular Biology 3: article 6

Tanaka A, Tapper B A, Popay A, Parker E J, Scott B (2005) A symbiosis expressed non-ribosomal peptide synthetase from a mutualistic fungal endophyte of perennial ryegrass confers protection to the symbiotum from insect herbivory. Molecular Microbiology 57: 1036-1050

Tsai H F, Liu J S, Staben C, Christensen M J, Latch G C, Siegel M R, Schardl C L (1994). Evolutionary diversification of fungal endophytes of tall fescue grass by hybridization with *Epichloë* species. Proc. Natl. Acad. Sci. USA 91 (7): 2542-2546

Welty R E, Azevedo M D, Cooper T M (1987) Influence of moisture content, temperature, and length of storage on seed germination and survival of endophytic fungi in seeds of tall fescue and perennial ryegrass. Phytopathology 77: 893-900

Wilkinson H H, Siegel M R, Blankenship J D, Mallory A C, Bush L P, Schardl C L (2000). Contribution of fungal loline alkaloids to protection from aphids in a grass-endophyte mutualism. Molecular Plant Microbe Interactions 13: 1027-1033

Yates S G, Fenster J C, Bartell R J (1989) Assay of tall fescue seed extracts, fractions and alkaloids using the large milkweed bug. Journal of Agriculture and Food Chemistry 37: 354-357

Zejda J E, McDuffie H H, Dosman J A (1993) Epidemiology of health and safety risks in agriculture and related industries—Practical applications for rural physicians. Western Journal of Medicine 158: 56-63

Zhang, D X, Nagabhyru P, Blankenship J D, Schardl C L (2010) Are loline alkaloid levels regulated in grass endophytes by gene expression or substrate availability? Plant Signaling and Behavior 5 (11): 1419-22

| DESCRIPTION OF THE MICROORGANISM DEPOSITS MADE UNDER THE BUDAPEST TREATY  The following biological deposits have been made under the terms of the Budapest Treaty on the International Recognition of the Deposit of Micro-organisms for the Purposes of Patent Procedure. | | |
| --- | --- | --- |
| Deposit Identification Reference | International Depository Designation | Date of Deposit |
| AR 3002 | NRRL 50579 | 13 Oct. 2011 |
| AR 3005 | NRRL 50580 | 13 Oct. 2011 |
| AR 3007 | NRRL 67556 | 5 Feb. 2018 |
| AR 3042 | NRRL 67560 | 5 Feb. 2018 |

Certificates of Deposit and Statements of Viability for the above deposited micro-organisms are appended.

What we claim is:

1. A combination comprising an isolated strain of *Epichloë* endophyte and a non-endogenous host plant, wherein the endophyte comprises a B10 allele size of 188±0.8 base pairs (bp) and a B11 allele size of 112±0.8 bp.

2. The combination of claim 1, wherein the *Epichloë* endophyte comprises at least one additional SSR allele selected from the group consisting of ans016, ans019, ans033, ans036, egs027, egs031, ces0004, ces0022, ces0041, ces0054, ces0060, ces0061, ces0067, ces0075, ces0076, ces0078, ces0089, ces0093, ces0094, and ces0095, wherein ans016, ans019, ans033, ans036, egs027, egs031, ces0004, ces0022, ces0041, ces0054, ces0060, ces0061, ces0067, ces0075, ces0076, ces0078, ces0089, ces0093, ces0094, and ces0095 comprise 282, 204, 181, 286, 359, 259, 185, 209, 261, 261, 238, 162, 277, 243, 157, 310, 165, 145, 329 and 360 base pairs, ±0.8 base pairs, respectively.

3. The combination of claim 1, wherein the *Epichloë* endophyte comprises at least two additional SSR alleles, or at least 3, at least 4, at least 5, at least 6, at least 7, at least 8, at least 9, at least 10, at least 11, at least 12, at least 13, at least 14, at least 15, at least 16, at least 17, at least 18, at least 19 additional SSR alleles, or 20 additional SSR alleles, wherein the additional alleles are selected from the group consisting of ans016, ans019, ans033, ans036, egs027, egs031, ces0004, ces0022, ces0041, ces0054, ces0060, ces0061, ces0067, ces0075, ces0076, ces0078, ces0089, ces0093, ces0094, and ces0095, wherein each of the additional SSR alleles comprises 282, 204, 181, 286, 359, 259, 185, 209, 261, 261, 238, 162, 277, 243, 157, 310, 165, 145, 329 and 360 base pairs, ±0.8 base pairs, respectively.

4. The combination of claim 1, wherein the *Epichloë* endophyte comprises the following 22 SSR alleles: B10, B11, ans016, ans019, ans033, ans036, egs027, egs031, ces0004, ces0022, ces0041, ces0054, ces0060, ces0061, ces0067, ces0075, ces0076, ces0078, ces0089, ces0093, ces0094, and ces0095, wherein the 22 SSR alleles comprise 188, 112, 282, 204, 181, 286, 359, 259, 185, 209, 261, 261, 238, 162, 277, 243, 157, 310, 165, 145, 329 and 360 base pairs, ±0.8 base pairs, respectively.

5. The combination of claim 1, wherein the *Epichloë* endophyte produces in planta at least one indole diterpene alkaloid or at least one ergot alkaloid.

6. The combination of claim 1, wherein the *Epichloë* endophyte does not produce, in planta, more than about 0.1 mg/kg ergovaline or more than about 0.1 mg/kg lolitrem B or both, wherein mg/kg is by dry weight of the endophyte and the host plant infected with the endophyte.

7. The combination of claim 1, wherein the *Epichloë* endophyte is a species or strain of *Epichloë bromicola* or a hybrid strain of *E. bromicola* and another *Epichloë* species.

8. The combination of claim 1, wherein the *Epichloë* endophyte is selected from the group consisting of AR3002 (NRRL #50579), AR3005 (NRRL #50580), AR3007 (NRRL #67556), and AR3042 (NRRL #67569) or combinations thereof.

9. The combination of claim 1, wherein the host plant is a grass plant or part thereof.

10. The combination of claim 1, wherein the host plant is a wheat plant or part thereof.

11. The combination of claim 10, wherein the part thereof of the host plant is a plant cell line or plant callus.

12. A method of making a stable host plant/*Epichloë* endophyte combination that produces at least one indole diterpene alkaloid or at least one ergot alkaloid comprising artificially infecting a non-endogenous host plant with an isolated strain of *Epichloë* endophyte, wherein the combination produces at least one indole diterpene alkaloid or at least one ergot alkaloid, and wherein the endophyte comprises a B10 allele size of 188±0.8 base pairs (bp) and a B11 allele size of 112±0.8 bp.

13. The method of claim 12, wherein the *Epichloë* endophyte comprises at least one additional SSR allele selected from the group consisting of ans016, ans019, ans033, ans036, egs027, egs031, ces0004, ces0022, ces0041, ces0054, ces0060, ces0061, ces0067, ces0075, ces0076, ces0078, ces0089, ces0093, ces0094, and ces0095, wherein ans016, ans019, ans033, ans036, egs027, egs031, ces0004, ces0022, ces0041, ces0054, ces0060, ces0061, ces0067, ces0075, ces0076, ces0078, ces0089, ces0093, ces0094, and ces0095 comprise 282, 204, 181, 286, 359, 259, 185, 209, 261, 261, 238, 162, 277, 243, 157, 310, 165, 145, 329 and 360 base pairs, ±0.8 base pairs, respectively.

14. The method of claim 12, wherein the *Epichloë* endophyte comprises at least two additional SSR alleles, or at least 3, at least 4, at least 5, at least 6, at least 7, at least 8, at least 9, at least 10, at least 11, at least 12, at least 13, at least 14, at least 15, at least 16, at least 17, at least 18, at least 19 additional SSR alleles, or 20 additional SSR alleles, wherein the additional alleles are selected from the group consisting of ans016, ans019, ans033, ans036, egs027, egs031, ces0004, ces0022, ces0041, ces0054, ces0060, ces0061, ces0067, ces0075, ces0076, ces0078, ces0089, ces0093, ces0094, and ces0095, wherein each of the additional SSR alleles comprises 282, 204, 181, 286, 359, 259, 185, 209, 261, 261, 238, 162, 277, 243, 157, 310, 165, 145, 329 and 360 base pairs, ±0.8 base pairs.

15. The method of claim 12, wherein the *Epichloë* endophyte comprises the following 22 SSR alleles: B10, B11, ans016, ans019, ans033, ans036, egs027, egs031, ces0004, ces0022, ces0041, ces0054, ces0060, ces0061, ces0067, ces0075, ces0076, ces0078, ces0089, ces0093, ces0094, and ces0095, wherein the 22 SSR alleles comprise 188, 112, 282, 204, 181, 286, 359, 259, 185, 209, 261, 261, 238, 162, 277, 243, 157, 310, 165, 145, 329 and 360 base pairs, ±0.8 base pairs, respectively.

16. The method of claim 12, wherein the *Epichloë* endophyte does not produce, in planta, more than about 0.1 mg/kg ergovaline or more than about 0.1 mg/kg lolitrem B or both, wherein mg/kg is by dry weight of the endophyte and the host plant infected with the endophyte.

17. The method of claim 12, wherein the *Epichloë* endophyte is a species or strain of *Epichloë bromicola* or a hybrid strain of *E. bromicola* and another *Epichloë* species.

18. The method of claim 12, wherein the *Epichloë* endophyte is selected from the group consisting of AR3002 (NRRL #50579), AR3005 (NRRL #50580), AR3007 (NRRL #67556), and AR3042 (NRRL #67569) or combinations thereof.

19. The method of claim 12, wherein the host plant is a grass plant or part thereof.

20. The method of claim 12, wherein the host plant is a wheat plant or part thereof.

21. The method of claim 20, wherein the part thereof of the host plant is a plant cell line or plant callus.

* * * * *